(12) United States Patent
Bladen et al.

(10) Patent No.: US 7,174,202 B2
(45) Date of Patent: *Feb. 6, 2007

(54) MEDICAL NAVIGATION APPARATUS

(75) Inventors: John Stuart Bladen, Sheffield (GB); Alan Patrick Anderson, Sheffield (GB)

(73) Assignee: British Telecommunications, London (GB)

( * ) Notice: Subject to any disclaimer, the term of this patent is extended or adjusted under 35 U.S.C. 154(b) by 256 days.

This patent is subject to a terminal disclaimer.

(21) Appl. No.: 10/320,658

(22) Filed: Dec. 17, 2002

(65) Prior Publication Data

US 2003/0163037 A1 Aug. 28, 2003

Related U.S. Application Data

(60) Continuation of application No. 09/489,340, filed on Jan. 21, 2000, now Pat. No. 6,522,907, which is a division of application No. 09/336,723, filed on Jun. 21, 1999, now Pat. No. 6,757,557, which is a division of application No. 08/392,955, filed as application No. PCT/GB93/01736 on Aug. 16, 1993, now Pat. No. 5,913,820.

(30) Foreign Application Priority Data

Jan. 27, 1993 (GB) .................... 9301569.1
Aug. 14, 1993 (EP) .................... 923074926

(51) Int. Cl.
*A61B 5/05* (2006.01)
(52) U.S. Cl. .............. 600/424; 600/117; 600/427; 702/153; 324/207.17
(58) Field of Classification Search .............. 600/407, 600/424, 117, 427; 128/899; 324/207.17, 324/207.26, 247; 702/152, 153
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |

(Continued)

FOREIGN PATENT DOCUMENTS

CA 964149 3/1975

(Continued)

OTHER PUBLICATIONS

"Prestige Cervical Disc System Surgical Technique", 12 pgs.

(Continued)

*Primary Examiner*—Ruth S. Smith
(74) *Attorney, Agent, or Firm*—Nixon & Vanderhye P.C.

(57) ABSTRACT

Methods and apparatus are provided for locating the position, preferably in three dimensions, of a sensor by generating magnetic fields which are detected at the sensor. The magnetic fields are generated from a plurality of locations and, in one embodiment of the invention, enable both the orientation and location of a single coil sensor to be determined. The present invention thus finds application in many areas where the use of prior art sensors comprising two or more mutually perpendicular coils is inappropriate.

85 Claims, 10 Drawing Sheets

U.S. PATENT DOCUMENTS

| | | |
|---|---|---|
| 3,061,936 A | 11/1962 | Dobbeleer |
| 3,073,310 A | 1/1963 | Mocarski |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,674,014 A | 7/1972 | Tilander |
| 3,702,935 A | 11/1972 | Carey et al. |
| 3,704,707 A | 12/1972 | Halloran |
| 3,868,565 A | 2/1975 | Kuipers |
| 3,941,127 A | 3/1976 | Froning |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,202,349 A | 5/1980 | Jones |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,328,813 A | 5/1982 | Ray |
| 4,339,953 A | 7/1982 | Iwasaki |
| 4,358,856 A | 11/1982 | Stivender et al. |
| 4,368,536 A | 1/1983 | Pfeiler |
| 4,396,885 A | 8/1983 | Constant |
| 4,403,321 A | 9/1983 | Kruger |
| 4,418,422 A | 11/1983 | Richter et al. |
| 4,422,041 A | 12/1983 | Lienau |
| 4,431,005 A | 2/1984 | McCormick |
| 4,485,815 A | 12/1984 | Amplatz |
| 4,543,959 A | 10/1985 | Sepponen |
| 4,548,208 A | 10/1985 | Niemi |
| 4,572,198 A | 2/1986 | Codrington |
| 4,584,577 A | 4/1986 | Temple |
| 4,613,866 A | 9/1986 | Blood |
| 4,618,978 A | 10/1986 | Cosman |
| 4,621,628 A | 11/1986 | Bludermann |
| 4,625,718 A | 12/1986 | Olerud et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,673,352 A | 6/1987 | Hansen |
| 4,706,665 A | 11/1987 | Gouda |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,727,565 A | 2/1988 | Ericson |
| 4,737,794 A | 4/1988 | Jones |
| 4,737,921 A | 4/1988 | Goldwasser et al. |
| 4,750,487 A | 6/1988 | Zanetti |
| 4,771,787 A | 9/1988 | Wurster et al. |
| 4,791,934 A | 12/1988 | Brunnett |
| 4,793,355 A | 12/1988 | Crum et al. |
| 4,797,907 A | 1/1989 | Anderton |
| 4,803,976 A | 2/1989 | Frigg et al. |
| 4,821,206 A | 4/1989 | Arora |
| 4,821,730 A | 4/1989 | Martinelli et al. |
| 4,821,731 A | 4/1989 | Martinelli et al. |
| 4,836,778 A | 6/1989 | Baumrind et al. |
| 4,845,771 A | 7/1989 | Wislocki et al. |
| 4,849,692 A | 7/1989 | Blood |
| 4,862,893 A | 9/1989 | Martinelli |
| 4,889,526 A | 12/1989 | Rauscher et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,131,397 A * | 7/1992 | Crowley ..................... 600/463 |
| 5,142,930 A | 9/1992 | Allen et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,628 A | 3/1993 | Hill, III et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,228,442 A | 7/1993 | Imran |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,291,199 A | 3/1994 | Overman et al. |
| 5,295,483 A | 3/1994 | Nowacki et al. |
| 5,297,549 A | 3/1994 | Beatty et al. |
| 5,299,254 A | 3/1994 | Dancer et al. |
| 5,299,288 A | 3/1994 | Glassman et al. |

| | | | | | |
|---|---|---|---|---|---|
| 5,305,091 A | 4/1994 | Gelbart et al. | 5,546,949 A | 8/1996 | Frazin et al. |
| 5,305,203 A | 4/1994 | Raab | 5,546,951 A | 8/1996 | Ben-Haim |
| 5,309,913 A | 5/1994 | Kormos et al. | 5,551,429 A | 9/1996 | Fitzpatrick et al. |
| 5,315,630 A | 5/1994 | Sturm et al. | 5,558,091 A | 9/1996 | Acker et al. |
| 5,316,024 A | 5/1994 | Hirschi et al. | 5,568,809 A | 10/1996 | Ben-Haim |
| 5,318,025 A | 6/1994 | Dumoulin et al. | 5,572,999 A | 11/1996 | Funda et al. |
| 5,320,111 A | 6/1994 | Livingston | 5,573,533 A | 11/1996 | Strul |
| 5,325,728 A | 7/1994 | Zimmerman et al. | 5,575,794 A | 11/1996 | Walus et al. |
| 5,325,873 A | 7/1994 | Hirschi et al. | 5,583,909 A | 12/1996 | Hanover |
| 5,329,944 A | 7/1994 | Fabian et al. | 5,588,430 A | 12/1996 | Bova et al. |
| 5,333,168 A | 7/1994 | Fernandes et al. | 5,592,939 A | 1/1997 | Martinelli |
| 5,353,795 A | 10/1994 | Souza et al. | 5,595,193 A | 1/1997 | Walus et al. |
| 5,353,800 A | 10/1994 | Pohndorf et al. | 5,596,228 A | 1/1997 | Anderton et al. |
| 5,353,807 A | 10/1994 | DeMarco | 5,600,330 A | 2/1997 | Blood |
| 5,368,030 A | 11/1994 | Zinreich et al. | 5,603,318 A | 2/1997 | Heilbrun et al. |
| 5,375,596 A | 12/1994 | Twiss et al. | 5,617,462 A | 4/1997 | Spratt |
| 5,377,678 A | 1/1995 | Dumoulin et al. | 5,617,857 A | 4/1997 | Chader et al. |
| 5,383,454 A | 1/1995 | Bucholz | 5,619,261 A | 4/1997 | Anderton |
| 5,385,146 A | 1/1995 | Goldreyer | 5,622,169 A | 4/1997 | Golden et al. |
| 5,385,148 A | 1/1995 | Lesh et al. | 5,622,170 A | 4/1997 | Schulz |
| 5,386,828 A | 2/1995 | Owens et al. | 5,627,873 A | 5/1997 | Hanover et al. |
| 5,389,101 A | 2/1995 | Heilbrun et al. | 5,628,315 A | 5/1997 | Vilsmeier et al. |
| 5,391,199 A | 2/1995 | Ben-Haim | 5,630,431 A | 5/1997 | Taylor |
| 5,394,457 A | 2/1995 | Leibinger et al. | 5,636,644 A | 6/1997 | Hart et al. |
| 5,397,329 A | 3/1995 | Allen | 5,638,819 A | 6/1997 | Manwaring et al. |
| 5,399,146 A | 3/1995 | Nowacki et al. | 5,640,170 A | 6/1997 | Anderson |
| 5,400,384 A | 3/1995 | Fernandes et al. | 5,642,395 A | 6/1997 | Anderton et al. |
| 5,402,801 A | 4/1995 | Taylor et al. | 5,643,268 A | 7/1997 | Vilsmeier et al. |
| 5,408,409 A | 4/1995 | Glassman et al. | 5,645,065 A | 7/1997 | Shapiro et al. |
| 5,417,210 A | 5/1995 | Funda et al. | 5,647,361 A | 7/1997 | Damadian |
| 5,419,325 A | 5/1995 | Dumoulin et al. | 5,662,111 A | 9/1997 | Cosman |
| 5,423,334 A | 6/1995 | Jordan | 5,664,001 A | 9/1997 | Tachibana et al. |
| 5,425,367 A | 6/1995 | Shapiro et al. | 5,674,296 A | 10/1997 | Bryan et al. |
| 5,425,382 A | 6/1995 | Golden et al. | 5,676,673 A | 10/1997 | Ferre et al. |
| 5,426,683 A | 6/1995 | O'Farrell, Jr. et al. | 5,681,260 A | 10/1997 | Ueda et al. |
| 5,426,687 A | 6/1995 | Goodall et al. | 5,682,886 A | 11/1997 | Delp et al. |
| 5,427,097 A | 6/1995 | Depp | 5,687,737 A * | 11/1997 | Branham et al. ............ 600/523 |
| 5,429,132 A | 7/1995 | Guy et al. | 5,690,108 A | 11/1997 | Chakeres |
| 5,433,198 A | 7/1995 | Desai | 5,694,945 A | 12/1997 | Ben-Haim |
| RE35,025 E | 8/1995 | Anderton | 5,695,501 A | 12/1997 | Carol et al. |
| 5,437,277 A | 8/1995 | Dumoulin et al. | 5,697,056 A | 12/1997 | Taylor et al. |
| 5,443,066 A | 8/1995 | Dumoulin et al. | 5,697,377 A | 12/1997 | Wittkampf |
| 5,443,489 A | 8/1995 | Ben-Haim | 5,702,406 A | 12/1997 | Vilsmeier et al. |
| 5,444,756 A | 8/1995 | Pai et al. | 5,711,299 A | 1/1998 | Manwaring et al. |
| 5,445,144 A | 8/1995 | Wodicka et al. | 5,713,946 A | 2/1998 | Ben-Haim |
| 5,445,150 A | 8/1995 | Dumoulin et al. | 5,715,822 A | 2/1998 | Watkins |
| 5,445,166 A | 8/1995 | Taylor | 5,715,836 A | 2/1998 | Kliegis et al. |
| 5,446,548 A | 8/1995 | Gerig et al. | 5,718,241 A | 2/1998 | Ben-Haim et al. |
| 5,447,154 A | 9/1995 | Cinquin et al. | 5,727,552 A | 3/1998 | Ryan |
| 5,448,610 A | 9/1995 | Yamamoto et al. | 5,727,553 A | 3/1998 | Saad |
| 5,453,686 A | 9/1995 | Anderson | 5,729,129 A | 3/1998 | Acker |
| 5,456,718 A | 10/1995 | Szymaitis | 5,730,129 A | 3/1998 | Darrow et al. |
| 5,458,718 A | 10/1995 | Venkitachalam | 5,730,130 A | 3/1998 | Fitzpatrick et al. |
| 5,464,446 A | 11/1995 | Dreessen et al. | 5,732,703 A | 3/1998 | Kalfas et al. |
| 5,478,341 A | 12/1995 | Cook et al. | 5,735,278 A | 4/1998 | Hoult et al. |
| 5,478,343 A | 12/1995 | Ritter | 5,738,096 A | 4/1998 | Ben-Haim |
| 5,480,422 A | 1/1996 | Ben-Haim | 5,741,214 A | 4/1998 | Ouchi et al. |
| 5,483,961 A | 1/1996 | Kelly et al. | 5,742,394 A | 4/1998 | Hansen |
| 5,485,849 A | 1/1996 | Panescu et al. | 5,744,953 A | 4/1998 | Hansen |
| 5,487,391 A | 1/1996 | Panescu | 5,748,767 A | 5/1998 | Raab |
| 5,487,729 A | 1/1996 | Avellanet et al. | 5,749,362 A | 5/1998 | Funda et al. |
| 5,487,757 A | 1/1996 | Truckai et al. | 5,749,835 A | 5/1998 | Glantz |
| 5,490,196 A | 2/1996 | Rudich et al. | 5,752,513 A | 5/1998 | Acker et al. |
| 5,494,034 A | 2/1996 | Schlondorff et al. | 5,755,725 A | 5/1998 | Druais |
| 5,503,416 A | 4/1996 | Aoki et al. | RE35,816 E | 6/1998 | Schulz |
| 5,513,637 A | 5/1996 | Twiss et al. | 5,758,667 A | 6/1998 | Slettenmark |
| 5,515,160 A | 5/1996 | Schulz et al. | 5,762,064 A | 6/1998 | Polyani |
| 5,517,990 A | 5/1996 | Kalfas et al. | 5,767,669 A | 6/1998 | Hansen et al. |
| 5,531,227 A | 7/1996 | Schneider | 5,769,789 A | 6/1998 | Wang et al. |
| 5,531,520 A | 7/1996 | Grimson et al. | 5,769,861 A | 6/1998 | Vilsmeier |
| 5,542,938 A | 8/1996 | Avellanet et al. | 5,772,594 A | 6/1998 | Barrick |
| 5,543,951 A | 8/1996 | Moehrmann | 5,775,322 A | 7/1998 | Silverstein et al. |
| 5,546,940 A | 8/1996 | Panescu et al. | 5,776,064 A | 7/1998 | Kalfas et al. |

| | | |
|---|---|---|
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,728 A | 9/1998 | Kuhn |
| 5,810,735 A | 9/1998 | Halperin et al. |
| 5,823,192 A | 10/1998 | Kalend et al. |
| 5,823,958 A | 10/1998 | Truppe |
| 5,828,725 A | 10/1998 | Levinson |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,884,410 A | 3/1999 | Prinz |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schultz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,981 A | 9/1999 | Cosman |
| 5,950,629 A | 9/1999 | Taylor et al. |
| 5,951,475 A | 9/1999 | Gueziec et al. |
| 5,954,647 A | 9/1999 | Bova et al. |
| 5,964,796 A | 10/1999 | Imran |
| 5,967,980 A | 10/1999 | Ferre et al. |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,052,610 A | 4/2000 | Koch |
| 6,059,718 A | 5/2000 | Taniguchi et al. |
| 6,063,022 A | 5/2000 | Ben-Haim |
| 6,073,043 A | 6/2000 | Schneider |
| 6,104,944 A | 8/2000 | Martinelli |
| 6,118,845 A | 9/2000 | Simon et al. |
| 6,122,538 A | 9/2000 | Sliwa, Jr. et al. |
| 6,131,396 A | 10/2000 | Duerr et al. |
| 6,139,183 A | 10/2000 | Graumann |
| 6,149,592 A | 11/2000 | Yanof et al. |
| 6,156,067 A | 12/2000 | Bryan et al. |
| 6,161,032 A | 12/2000 | Acker |
| 6,167,296 A | 12/2000 | Shahidi |
| 6,172,499 B1 | 1/2001 | Ashe |
| 6,175,756 B1 | 1/2001 | Ferre et al. |
| 6,233,476 B1 | 3/2001 | Strommer et al. |
| 6,223,067 B1 | 4/2001 | Vilsmeier |
| 6,246,231 B1 | 6/2001 | Ashe |
| 6,273,896 B1 | 8/2001 | Franck et al. |
| 6,298,262 B1 | 10/2001 | Franck et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,381,485 B1 | 4/2002 | Hunter et al. |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,527,443 B1 | 3/2003 | Vilsmeier et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,179 B1 | 3/2004 | Martinelli et al. |

FOREIGN PATENT DOCUMENTS

| | | |
|---|---|---|
| DE | 3042343 A1 | 6/1982 |
| DE | 3831278 A1 | 3/1989 |
| DE | 4233978 C1 | 4/1994 |
| DE | 10085137 | 11/2002 |
| EP | 0038151 | 10/1981 |
| EP | 0 319 844 A1 | 1/1988 |
| EP | 0350996 A1 | 1/1990 |
| EP | 0 651 968 A1 | 8/1990 |
| EP | 0399536 | 11/1990 |
| EP | 0419729 A1 | 8/1991 |
| EP | 0 581 704 B1 | 7/1993 |
| EP | 0894473 A2 | 1/1995 |
| EP | 0655138 B1 | 5/1995 |
| FR | 2417970 | 2/1979 |
| JP | 2765738 | 4/1998 |
| WO | WO 88/09515 | 12/1988 |
| WO | WO 89/05123 | 6/1989 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92 06645 A1 | 4/1992 |
| WO | WO 93/04628 | 3/1993 |
| WO | WO 94/04938 | 3/1994 |
| WO | WO 94/23647 | 10/1994 |
| WO | WO 94/24933 | 11/1994 |
| WO | WO 96/11624 | 4/1996 |
| WO | WO 98/08554 | 3/1998 |
| WO | WO 98/38908 | 9/1998 |
| WO | WO 99/60939 | 12/1999 |

WO WO 01/30437 A1 5/2001

OTHER PUBLICATIONS

Adams et al., "Orientation Aid for Head and Neck Surgeons," Innov. Tech. Biol. Med., vol. 13, No. 4, 1992, pp. 409-424.
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Willis Nail in Acute Fractures of the Femur," Journal of Orthopaedic Trauma, vol. 6, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitsky et al., "Three-Dimensional Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2 (Aug. 1993), pp. 252-259.
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Bryan, "Bryan Cervical Disc System Single Level Surgical Technique", Spinal Dynamics, 2002, pp. 1-33.
Bucholz et al., "Variables affecting the accuracy of stereotactic localizationusing computerized temography," Journal of Neurosurgery, vol. 79, Nov. 1993, pp. 667-673.
Champleboux et al., "Accurate Calibration of Cameras and Range Imaging Sensors: the NPBS method," IEEE International Conference on Robotics and Automation, Nice, France, May, 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Gildenberg et al., "Calculation of Stereotactic Coordinates from the Computed Tomographic Scan," Neurosurgery, vol. 10, No. 5, May 1982, pp. 580-586.
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. '96, pp. 42-51.
Gueziec et al., "Registration of Computed Tomography Data to a Surgical Robot Using Fluoroscopy: A Feasibility Study," Computer Science/Mathematics, Sep. 27, 1996, 6 pages.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hatch, "Reference-Display System for the Integration of CT Scanning and the Operating Microscope," Thesis, Thayer School of Engineering, Oct. 1984, pp. 1-189.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol.53, Dec. 1980, pp. 816-820.
Joskowicz et al., "Computer-Aided Image-Guided Bone Fracture Surgery: Concept and Implementation," CAR '98, pp. 710-715.
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Laitinen et al., "An Adapter for Computed Tomography-Guided, Stereotaxis," Surg. Neurol., 1985, pp. 559-566.
Laitinen et al., "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique for Accurate Transpedicular Screw Fixation Using CT Data and a 3-D Optical Localizer," TIMC, Faculte de Medecine de Grenoble.
Lavallee et al., "Image guided operating robot: a clinical application in stereotactic neurosurgery," Proceedings of the 1992 IEEE Internation Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, "VI Adaption de la Methodologie a Quelques Applications Cliniques," Chapitre VI, pp. 133-148.
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Col. Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Application au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545.549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microstereotaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382 (4 unnumbered pp.).

Smith et al., "The Neurostation ™--A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6.

Viant et al., "A Computer Assisted Orthopaedic System for Distal Locking of Intramedullary Nails," Proc. of MediMEC '95, Bristol, 1995, pp. 86-91.

* cited by examiner (a)

(b)

MEDICAL NAVIGATION APPARATUS

This is a continuation of application Ser. No. 09/489,340 filed Jan. 21, 200 (now U.S. Pat. 6,522,907), which is, in turn, a divisional of application Ser. No. 09/336,723, filed Jun. 21, 1999 (now U.S. Pat. No. 6,757,557) which, in urn, is a divisional of application Ser. No. 08/392,955 filed May 30, 1995 (now U.S. Pat. No. 5,913,820) which is a 371 of PCI/GB 9301736 filed Aug. 16, 1993.

The present invention relates to methods of and apparatus for, determining the location of an object and in particular, but not exclusively to methods and apparatus which employ a magnetic field which is sensed at the object.

BACKGROUND OF THE INVENTION

It has been long appreciated that if the magnetic field around a: field generating element, for example a generating coil, can be accurately mapped then it might be possible to determine the location of a field sensor, for example a sensing coil, relative to the generating coil, from the signals sensed by such a sensing coil. However, a problem associated with doing this is that there are in general many locations and/or orientations of the sensing coil within the field of the generating coil that will provide the same characteristic sensing signals in the sensing coil. In order to use a magnetic field for this purpose, additional information must therefore be provided.

Prior art approaches to providing the additional information required comprise either moving the generating and sensing coils relative to each other, or scanning the axis of the generated field past the sensing coil.

An example of the first approach is taught in U.S. Pat. No. 3,644,825 wherein a system is disclosed for locating the position of a field sensor, comprising two orthogonal sensing coils, relative to a field generating element which relies on having knowledge of the direction of motion of the sensor relative to the generator. It should be noted that this system cannot detect the location of an object unless there is such relative motion, and its direction is known.

The second approach of scanning the axis of the generated field is disclosed, for position location in two dimensions, in U.S. Pat. No. 3,121,228 and for position location in three dimensions in U.S. Pat. No. 3,868,565.

U.S. Pat. No. 3,121,228 describes how the distance and direction of a sensor, again comprising two orthogonal sensing coils, relative to a field generator, also comprising two orthogonal coils, can be determined. The two orthogonal generating coils are driven in phase quadrature so that the axis of the resultant field is caused to rotate within a plane. If the sensor is located within this plane then the axis of the field is guaranteed to scan past the sensor, and, because at any given distance from a field generator the field strength will be a maximum at the field axis, the sensor will detect a maximum in field strength at this time. The voltage induced in any one of the two coils forming the sensor will be dependent on the orientation of the coil relative to the field generator, and it is for this reason that in '228 two orthogonal coils are utilised in the sensor. The sum of these two voltages gives an indication of the distance between the sensor and generator, while the phase difference between the two voltages gives an indication of the direction of the generator relative to the sensor. It is thus essential to the operation of the location system of '228 that the axis of the field rotates and that two coils are present in the sensor.

In U.S. Pat. No. 3,868,555 this approach of scanning the axis, or maximum intensity vector, of the field past the sensor is extended to allow location of the sensor in three dimensions. Whereas in two dimensions it is sufficient merely to rotate the axis of the field within the plane to be sensed to guarantee it passing through the sensor, in three dimensions the axis would have to be rotated so that it described the surface of a sphere in order to be certain it encountered the sensor. To ensure that the axis passed through all points on the surface of a sphere the motion of the axis would be such that it encountered the sensor only very infrequently, and thus measurements by the sensor of the maximum field strength would also be infrequent. To avoid this the location system of '565 drives the Generator coils in a complex fashion so that the field axis tracks and rotates around the position of the sensor.

In order to locate the position of the sensor in three dimensions, according to the method of '565, three mutually orthogonal generating coils and three mutually orthogonal sensing coils are required and the three generating coils must be driven simultaneously by the three drive currents having amplitude and phase relationships between them which are controlled so as to direct the field axis towards the sensor.

The approach taken in '565 further requires that the various equations governing the voltage induced in a sensing coil located and orientated in a particular alternating magnetic field are solved dynamically in real time ie. during the acquisition of data from the sensing coil. This requirement, in addition to limiting the speed at which the sensor can move while still being located successfully by the system, also means that should it be desired to locate more than one sensor, all apparatus will need to be duplicated for each additional sensor.

According to a first aspect of the present invention there is provided a method of determining the location and the orientation of a field sensor relative to a plurality of field generators of know location, each field generator comprising a plurality of collocated field generating elements, the method comprising the steps of:

1) for each generator, energising each generating element and measuring the respective element at the field sensor,
2) for each field generator calculating, from the measurements of the field generated by each of its generating elements and an estimate of the orientation of the sensor, an estimate of the distance from that particular field generator to the sensor,
3) utilising the estimates of the distances from each of the field generators to the sensor, and the known location of the field generators to calculate the location of the sensor relative to the field generators,
4) employing the estimated location of the sensor from step 3) and the measurements of the field at the sensor to calculate a new estimate of the orientation of the sensor, and
5) repeating steps 2) to 4) iteratively, with step 2) employing the new estimate of sensor orientation from the preceding step 4), to improve the estimates of location and orientation of the sensor.

The method of the first aspect of the present invention thus enables the location of a sensor to be determined without either relative motion between the sensor and the field generating element, or scanning of the axis of the field.

Since the method dissociates the stages of acquisition of data from the sensor, and processing of that data, rapid determination of the sensor location is facilitated. Furthermore the location of additional sensors may be determined simply by simultaneous measuring the field, generated by each generating element, at these other sensors and independently calculating their distances from the field generators. It should be noted that no modification of the field generating apparatus or method of driving the apparatus is required in order to determine the location of a plurality of sensors.

The applicants have discovered that advantageously the method of the first aspect of the present invention also allows the location of a sensor comprising a single sensing element, for example a sensing coil, to be determined, as will be explained subsequently. This is particularly advantageous for positioning applications in which two or more mutually orthogonal sensing coils, as required by prior art techniques, cannot be used.

According to a second aspect of the present invention there is provided a method of determining the location of a field sensor, comprising a plurality of collocated field sensing elements, relative to a field generator, comprising a plurality of collocated field generating elements, the method comprising the steps of:

1) energising a single field generating element to establish a field,
2) measuring a value of the field strength at the field sensor which is dependent on the location and orientation of the sensor within the field,
3) repeating steps 1) and 2) for each field generating element,
4) calculating, by utilising all the values measured in step 2 and an estimate of the direction of the sensor from the field generator, a direction dependent weighting factor for each field generating element so that the calculated field strength B is equal to the field strength B that would exist at the sensor if the axis of the field were directed towards the sensor,
5) iteratively altering the direction dependent weighting factors to maximise B and thus to determine to a desired level of accuracy the direction of the sensor from the field generator, and
6) employing the measured values of field strength to calculate the distance of the sensor from the field generator and have, from the direction of the sensor in step 5), the location of the sensor relative to the field generator.

This aspect of the invention thus provides a method of locating a sensor relative to a single field generator.

The invention further provides apparatus suitable for carrying out the methods of the first two aspects of the invention.

BRIEF DESCRIPTION OF THE DRAWINGS

Preferred embodiments of the present invention will now be described, by way of example only, with reference to the accompanying figures in which.

DETAILED DESCRIPTION OF THE DRAWINGS

Figure 1:
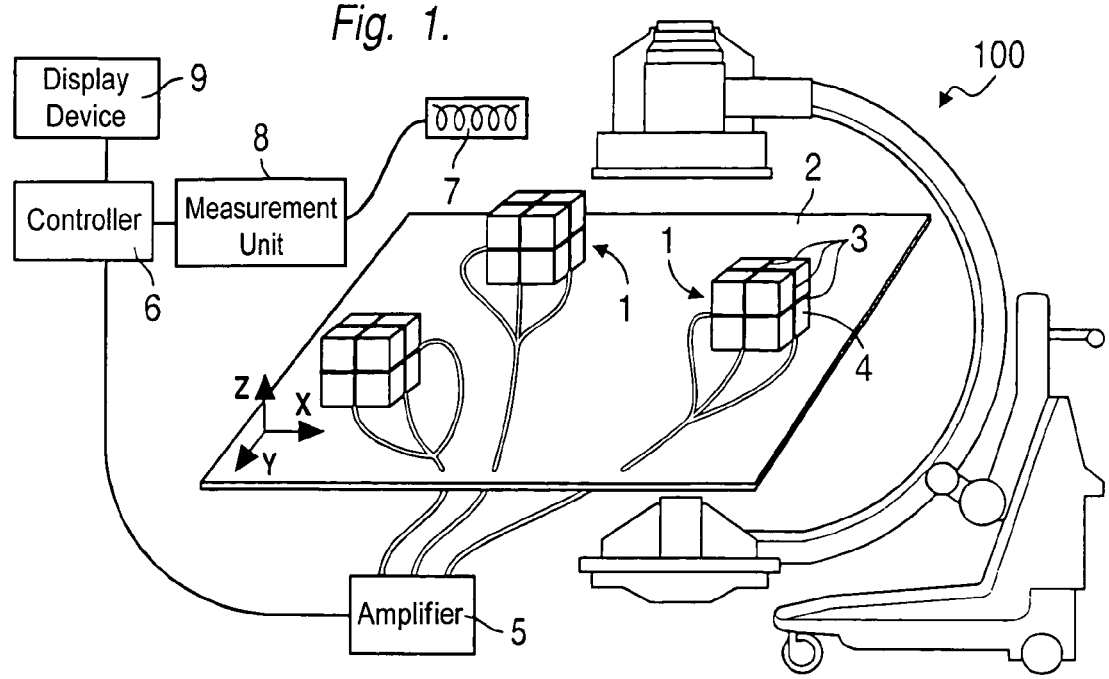
FIG. 1 shows a first embodiment of the invention.
Figure 14:
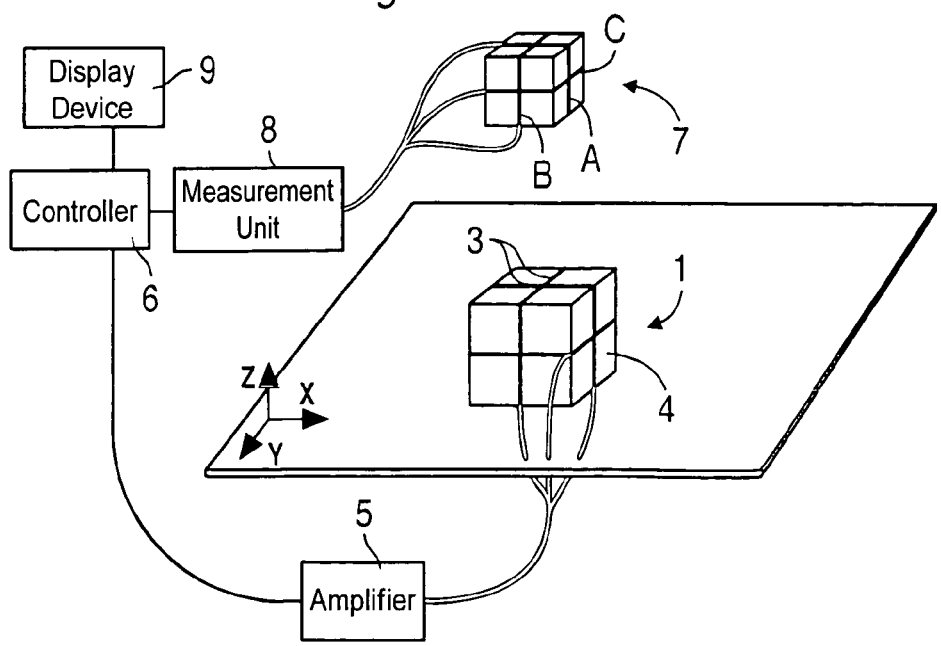
FIG. 14 shows a second embodiment of the invention.

With reference to FIG. 1, three field generators 1 are mounted at known locations on a plane surface 2. Each field generator 1 comprises three electrically separate coils of wire (generating coils) 3 wound about a cuboid wooden former 4, which is approximately 40 mm along one side. The three coils of each field generator are wound so that the axes of the coils are mutually perpendicular. The nine generating coils are separately electrically connected to an amplifier 5 which is able, under the direction of a controller 6, to drive each of the coils individually. Each coil comprises 40 turns of 0.45 mm copper wire and has an inductance of approximately 75 µH.

The sensor 7 comprises a single sensing coil of 200 turns of 42 swg wire on a ferrite core of diameter 0.8 mm, and length 12 mm. Larger sensor coils will in general be more sensitive of the electro-magnetic fields generated by the generating coils, however the size of the coil is normally governed by the particular position location problem which is being addressed and frequently small sensor coils will be required. For an air-cored coil the sensitivity of the sensor depends on the area of the coil, however the sensitivity can be increased by utilising a high magnetic permeability material in the core, and in this case the sensitivity will depend more strongly on the length of the coil than on its diameter. The sensing coil is electrically connected to a measurement unit 8 which in turn is connected to the controller 6. The measurement unit 8 comprises an analogue to digital converter, and a matched filter (not shown).

In use, the controller 6 directs the amplifier 5 to drive each of the nine generating coils 3 sequentially. The amplifier 5 outputs a 10 kHz drive signal of 3 amps rms which causes the particular generating coil being driven to generate a quasi-static magnetic field. The frequency of the drive signal is chosen so that, within the range over which the location of the sensor is to be determined, the field generated is a near-field electromagnetic field i.e the wavelength is long compared to the distance from the generating coil to the sensing coil.

Furthermore the drive signal frequency must be chosen so as to provide a compromise between sensor coil sensitivity, and the detrimental effects of electromagnetic noise due to induced eddy currents within electrically conductive objects within the positioning range, since both of these aspects increase with frequency. In the absence of electrically conducting objects a frequency of several hundred kilohertz may be used giving good sensor sensitivity and thus good range and positioning accuracy. In the presence of highly conductive objects, this frequency may need to be reduced to a few hertz. In this case a sensor coil may no longer be appropriate and may be replaced by an alternative magnetic field sensor, such as a flux gate magnetometer. In this embodiment a drive frequency of 10 kHz has been found to be a suitable compromise between sensitivity and immunity to interference from electrically conductive objects.

Once the quasi-static field from a particular generating coil 3 is established, the value of the voltage induced in the sensing coil 7 by this field is measured by the measurement unit 8. The signal from the sensing coil 7 is first amplified and then sampled at 40 kHz by a 16 bit analogue-to-digital converter. The sampled signal is windowed using a Blackman-Harris window, the 10 kHz component is extracted by the matched filter and hence a value representing the voltage induced in the sensing coil 7 is established. This value is passed to the controller 6 which stores the value and then instructs the amplifier 5 to stop driving the present generating coil 3 and to start driving the next generating coil 3. When all nine generating coils 3 have been driven, or energised, and the corresponding nine voltages induced in the sensing coil 7 have been measured and stored, the controller 6 calculates the location and orientation of the sensor 7 relative to the field generators 1 and displays this on a display device 9. This calculation can be carried out while the subsequent set of nine measurements are being taken. Thus, by sequentially driving each of nine generating coils 3, arranged in three groups of three mutually orthogonal coils, the location and orientation of a single sensing coil 7 can be determined.

Figure 2:
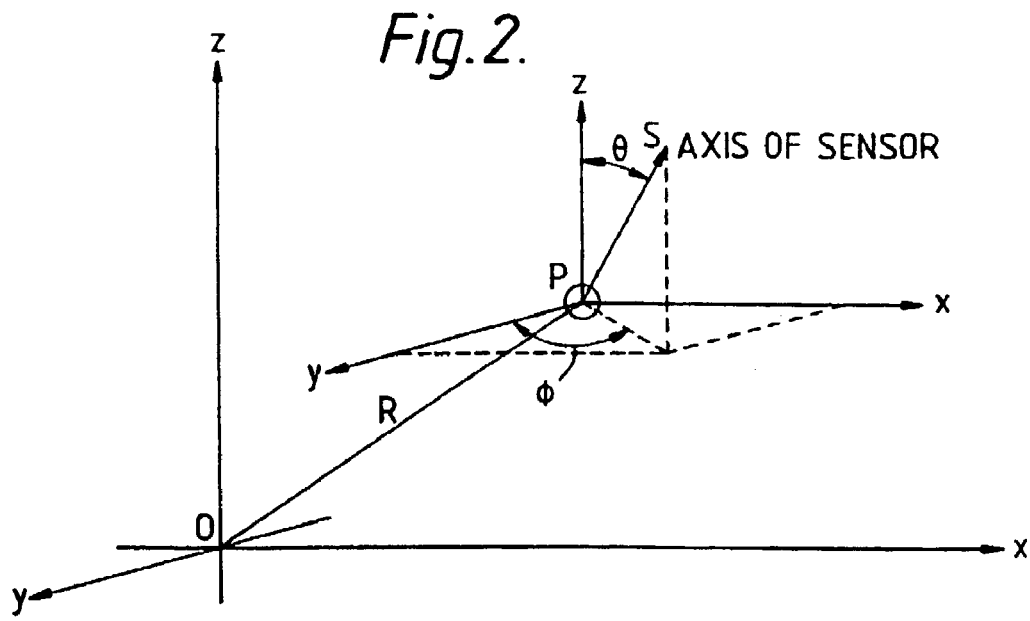
FIG. 2 shows the cartesian coordinate system employed for a sensor of arbitrary orientation located at point P.

In order to describe the algorithm employed by the controller 6 to calculate the location and orientation of the sensor 7, a coordinate system will first be defined. In FIG. 2 is shown a sensor, located at position P, whose axis is orientated along direction S. In general in order to determine the location and orientation of a single sensing coil within a field the x, y, z Cartesian coordinates of the sensor and the elevation angle $\theta$, and rotational angle $\phi$, must be found (see FIG. 2). The vector distance R of the sensor from the origin, O, of the coordinate system is also shown in FIG. 2. Both the location and orientation of the sensing coil within the field will affect the voltage induced in the coil by the field, but rotation of the coil about its axis will not affect the induced voltage and thus does not constitute a further unknown quantity.

Figure 3:
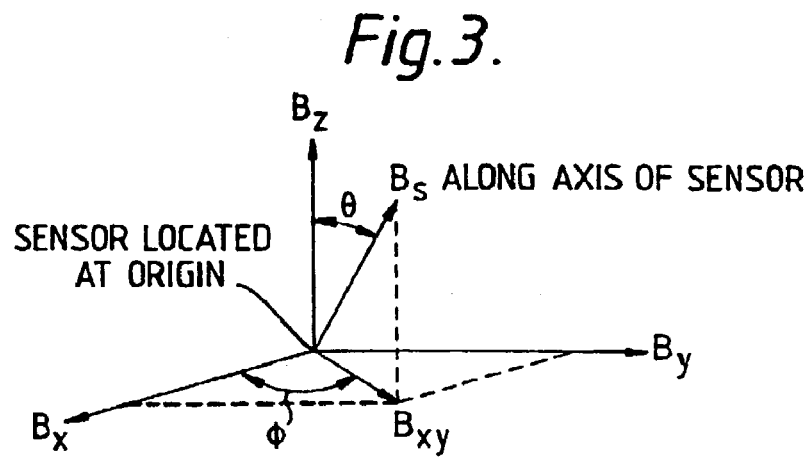
FIG. 3 shows schematically the resolution of the magnetic flux density at a sensor.

Assuming now that a single field generating coil 3 is placed at the origin O of the coordinate system with its axis directed along the z-axis. When the generating coil is energised a field will be produced at the sensor location P which has a magnetic flux density B. With reference to FIG. 3 this magnetic flux B can be resolved along the three axes of the coordinate system to give Bx, By and Bz and subsequently resolved along the axis of the sensor thus:

$$B_{xy} = B_x \cos \phi + B_y \sin \phi \tag{1}$$

and $$B_s = B_z \cos \theta + B_{xy} \sin \theta \tag{2}$$

The voltage $V_s$, induced in the sensor is related to the flux density via $V_s = k_s B_s$ where $k_s$ is known and is a function of the frequency of the field and the characteristics of the sensing coil. It therefore follows from (1) and (2) that the voltage induced in the sensor at any x-y-z location and for any $\theta$–$\phi$ orientation is given by, $$V_s = k_s(B_z \cos \theta + \sin \theta (B_x \cos \phi + B_y \sin \phi)) \tag{3}$$

Formulae defining $B_x$, $B_y$ and $B_z$ are developed from standard near field electromagnetic theory. Upon substituting the terms for $B_x$, $B_y$ and $B_z$ from equations (A-12) to (A-14) below into (3), it can be shown that, wherein the $D_x$ and $D_y$ sub-suffices relate to the field generated by the $D_x$ and $D_y$ coils. Upon substituting (A-1) and (A-2) below (5) and (6) become, $$V_s = k_c k_s \left[ \frac{(2z^2 - x^2 - y^2)\cos\theta + 3z \sin\theta(x\cos\phi + y\sin\phi)}{(x^2 + y^2 + z^2)^{5/2}} \right] \tag{4}$$

where $k_c$ is known and is a function of the current through, diameter of, and number of turns on the generating coil. The five unknown quantities, x, y, z, $\theta$ and $\phi$ are evident in (4): all other variables are known.

Equation (4) has been derived, as stated above, for the case of a single generating coil 3 directed along the z-axis, there will of course be a corresponding equation for each of the three generating coils 3 of each of the three field generators 1.

It has been found that despite the complexity of this term (4) it is possible to determine the location and orientation of a single sensing coil by sequentially energising each generating coil. To explain this approach to position location the two dimensional case will first be considered.

Figure 4:
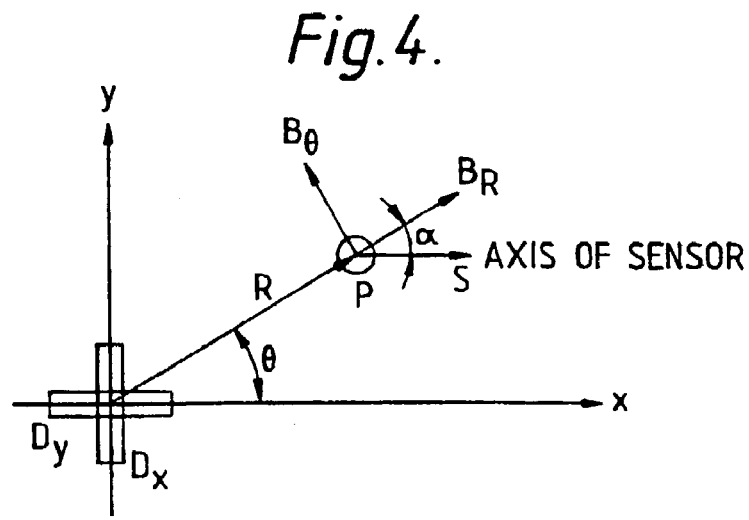
FIG. 4 shows the coordinate system employed to locate a sensor relative to a field generator.

FIG. 4 shows a field generator comprising two orthogonal field generating coils $D_x$ and $D_y$ located at the origin of the coordinate system. The single sensing coil sensor is located at P and its axis is parallel to direction S. The angle $\alpha$ is the angle between vector direction R of the sensor from the origin, and the direction S of the sensor axis.

The voltages induced in the sensor when coils $D_x$ and $D_y$ are energised sequentially are respectively $$V_{sDx} = k_s(B_{RDx}\cos \alpha - B_{sDx}\sin \alpha) \tag{5}$$

and $$V_{sDy} = k_s(B_{RDy}\cos \alpha + B_{sDy}\sin \alpha) \tag{6}$$

wherein the $D_x$ and $D_y$ sub-suffices relate to the field generated by the $D_x$ and $D_y$ coils. Upon substituting (A-1) and (A-2) below (5) and (6) become, $$V_{sDx} = \frac{K_c k_s}{R^3}(2\cos\theta\cos\alpha - \sin\theta\sin\alpha) \tag{7}$$

$$V_{sDy} = \frac{k_c k_s}{R^3}(2\sin\theta\cos\alpha + \cos\theta\sin\alpha) \tag{8}$$

It has been noticed that the value of $\sqrt{V_{sDx}^2+V_{sDy}^2}$ remains constant for a constant value of $\alpha$.

From (7) and (8) we can write, $$\sqrt{V_{sDx}-V_{sDy}^2} = \frac{k_c k_s}{R^3} \begin{bmatrix} 4\cos-\theta\cos-\alpha+\sin^2\theta\sin^2-\alpha- \\ 4\sin\theta\sin\alpha\cos\theta\cos\alpha+ \\ 4\sin^2\theta\cos^2\alpha+\cos^2\theta\sin^2\alpha+ \\ 4\sin\theta\cos\alpha\cos\theta\sin\alpha \end{bmatrix}^{1/2} \quad (9)$$

which reduces to, $$\sqrt{V_{sDx^2}+V_{sDy^2}} = \frac{k_c k_s}{R^3}\sqrt{1+3\cos^2\alpha} \quad (10)$$

Figure 5:
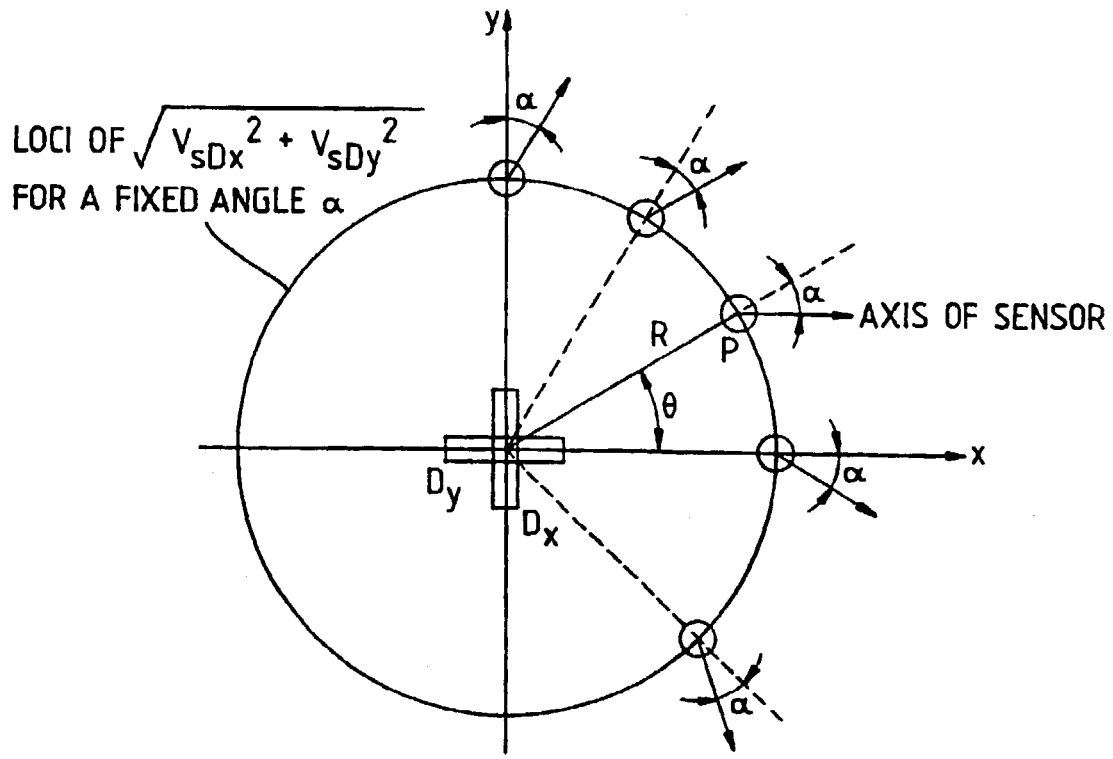
FIG. 5 shows schematically a simulated circle of constant induced voltage, in a sensor, in two dimensions, which is employed in the first embodiment of the invention

This can be thought of as corresponding physically to a circle of constant induced voltage in the sensor, centred on the field generator at the origin and lying in the x-y plane. This concept is shown schematically in FIG. 5. If the two individual measurements of induced voltage $V_{sDx}$ $V_{sDy}$ measured at the sensor are used to calculate $$\sqrt{V_{sDx}^2+V_{sDy}^2}$$

a circular or rotating field of constant strength can be simulated since $\sqrt{V_{sDx}^2+V_{sDy}^2}$ represents the maximum voltage that could be induced in the sensor if a rotating field were used. This is desirable since equation 10 gives a very simple relationship between R and $\alpha$.

The extension of this analysis to three dimensions is readily performed mathematically and conceptually very powerful because the approach taken does not require the axis of the generated field to be steered towards the sensor, but simply requires sequential energising of the individual generating coils. Thus for position determination in three dimensions of a single coil sensor, assuming three mutually perpendicular generating coils located at the origin of the coordinate system, we have $$\sqrt{V_{sDx^2}+V_{sDy^2}+V_{sDz^2}} = \frac{k_c k_s}{R^3}\sqrt{1+3\cos^2\alpha} \quad (11)$$

It should be noted that the term $\sqrt{1+3\cos^2\alpha}$ can only take values between 1 and 2, ignoring negative solutions and thus any value of R computed from (11) is only weakly dependent on the value of $\alpha$. For example, if $\alpha$ is assumed to be $\pi/2$ whereas its correct value is zero, the value of R computed from (11) is 80% of its correct value. This in fact represents the worst case scenario since $\alpha=0$ means $\sqrt{1+3\cos^2\alpha}=2$, while $\alpha=\pi/2$ means $\sqrt{1+3\cos^2\alpha}=1$.

Figure 6:
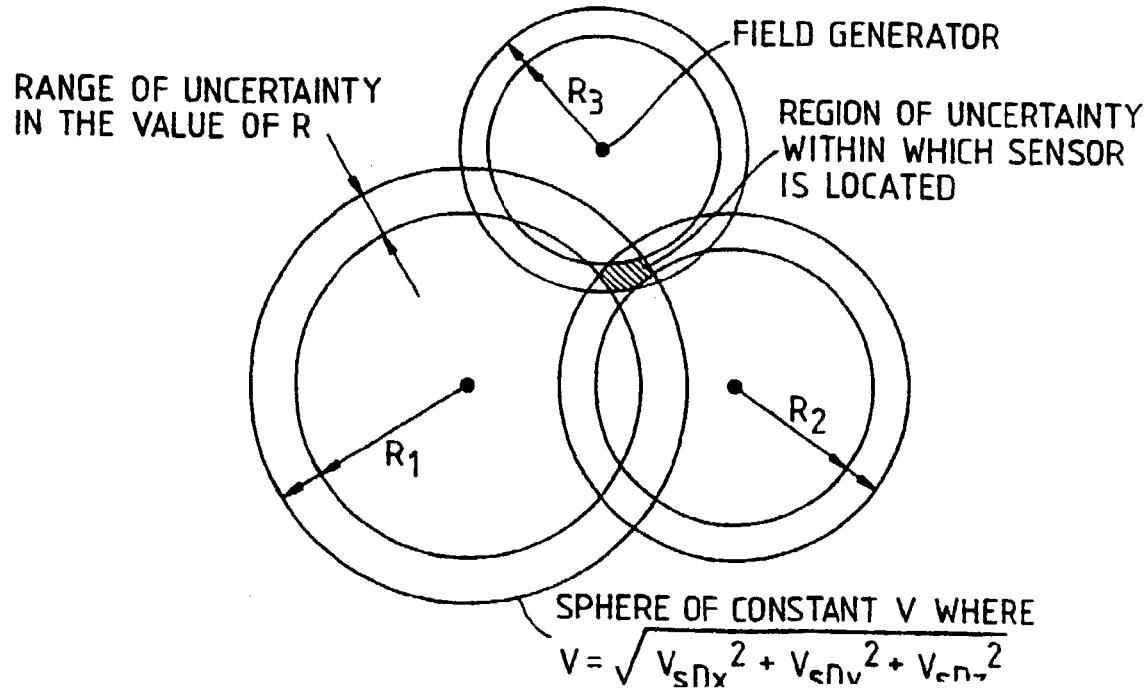
FIG. 6 shows schematically three simulated spheres of constant induced voltage each centred on a field generator, which is employed in the first embodiment of the invention.

Hence for each of three field generators a bounded value for R, the vector distance of the sensor from that particular field generator, can be calculated without any knowledge of the orientation $\alpha$ of the sensor. Since there are three field generators located at different known positions in the same plane (the x-y plane) and the distance R from each of them to the sensor has been calculated, the x-y-z coordinates of the sensor can be determined from simple trigonometry. This positioning methodology is shown schematically in FIG. 6. The three simulated spheres of constant induced voltage centred on each of the three field generators, and bounded by the potential error in R, overlap at two regions. One region is above the plane of the field generators and the other is below. In most applications, one solution is clearly erroneous and the location of the sensor can easily be uniquely determined.

At this stage the location of the sensor (but not its orientation) has been calculated to a limited degree of accuracy. For some applications this may be adequate, but in general the precise location and probably orientation of the sensor are required. This is achieved by the use of an iterative procedure in which the estimate of the x-y-z coordinates of the sensor, derived from the values of R for each of the three field generators, are used in the appropriate equation (4) for each of the nine generating coils to estimate values of $\theta$ and $\phi$ for the sensor, from these $\alpha$ is calculated for each of the three generators. Although $\theta$ and $\phi$ could be calculated from only two versions of equation (4), all nine versions are employed to improve the rate of convergence of the solution and its immunity from noise. The three values of $\alpha$ can then be invoked in the appropriate equation (11) for each field generator to calculate an improved estimate for R for each of the generators. This process is repeated, progressively reducing the error in R and $\alpha$ for each generator until the desired level of accuracy is achieved. It should be noted that this technique avoids the problems of non-convergence which would arise if equation (4) were utilised directly because a good estimate for R has been found before equation (4) is employed, and the estimate for R is bounded as shown schematically in FIG. 6.

Figure 7:
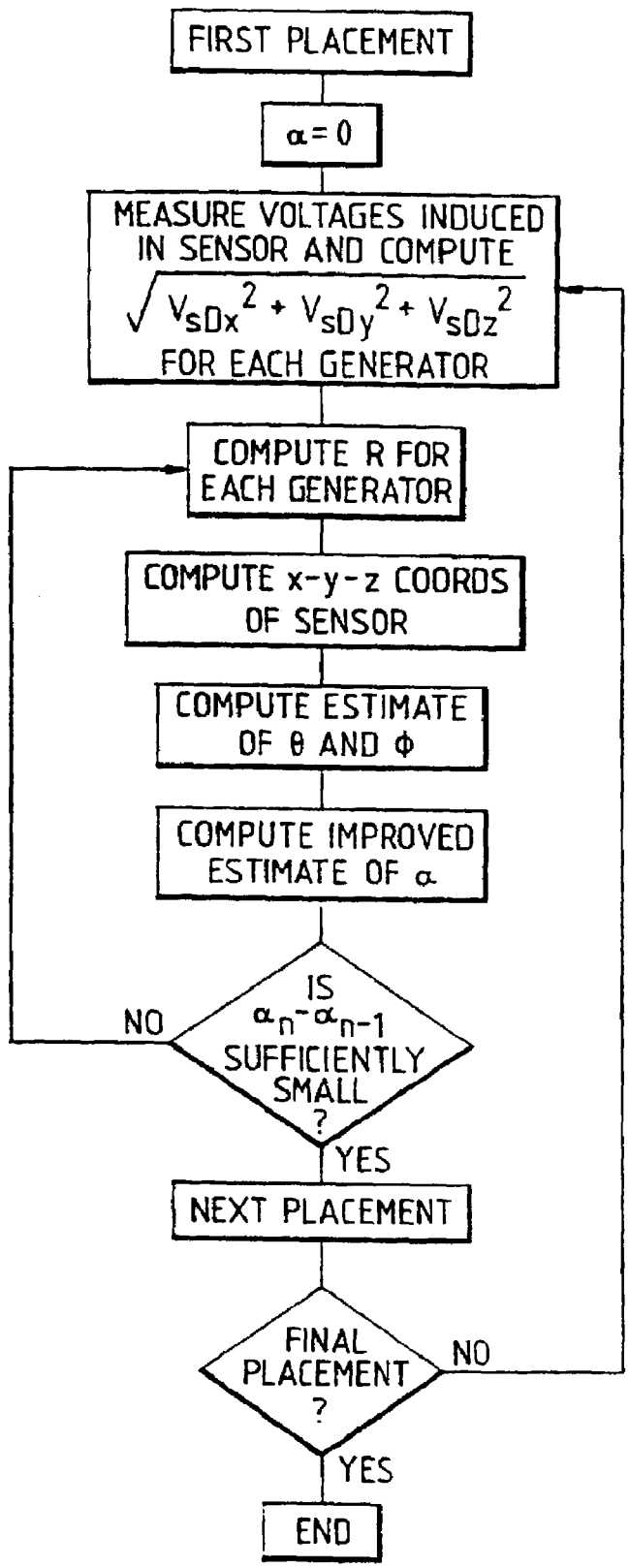
FIG. 7 shows a flow chart of a first positioning algorithm used in the first embodiment of the invention.

In summary, and with reference to FIG. 7, the algorithm utilised by the controller 6 is as follows:

1. Assume $\alpha=0$ initially. This ensures an over-estimate of R which guarantees an intersection of the radial distances from the three generator.
2. Measure the voltages induced in the sensor by each of the 9 individual generator coils, and then compute $\sqrt{V^2_{sDx}+V^2_{sDy}+V^2_{sDz}}$ for each of the three generators.
3. Invoke $\alpha$ in (11) and compute R for each of the three generators.
4. Compute the x-y-z coordinates of the sensor from the three values of R.
5. Invoke these coordinates in the appropriate version of equation (4) for each of the nine generating coils and compute an improved estimate of $\theta$ and $\phi$. This can be achieved by the use of, for example, the Gauss-Newton Least Squares optimisation technique.
6. Use the improved estimates of $\theta$ and $\phi$ to calculate $\alpha$ for each generator.
7. Return to step 3 until the difference between the new and previous estimates of $\alpha$ reaches a sufficiently low value commensurate with the required positional accuracy in the x-y-z coordinates being achieved.

Figure 8:
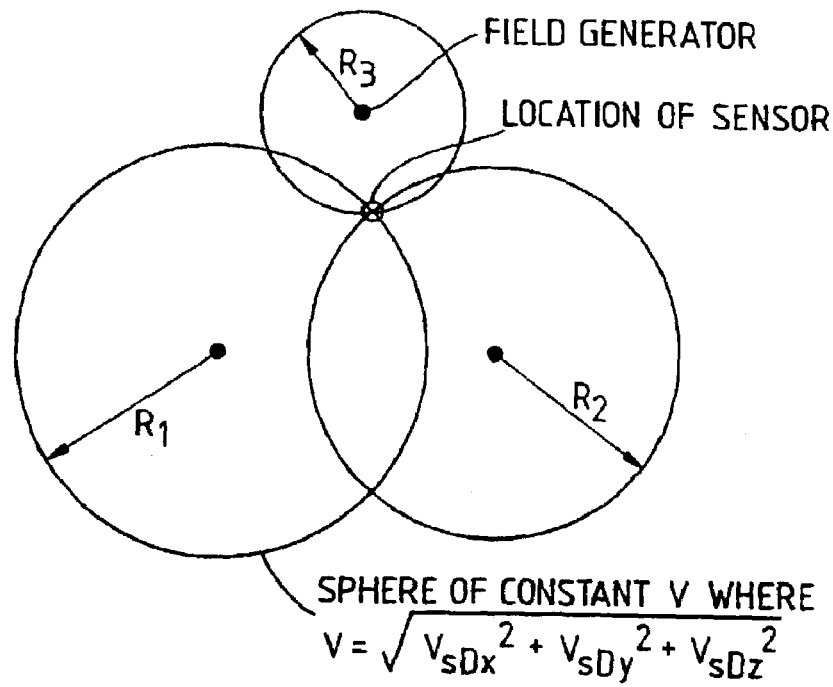
FIG. 8 shows the same schematic as FIG. 6 when the location and orientation of the sensor have been determined, FIGS. 9, 10 and 11 schematically show a coordinate system employed in a second positioning algorithm used in the first embodiment of the invention, FIGS. 12(*a*) to 12(*f*) show images of an endoscope obtained using the positioning system of the present invention on the left, and images obtained conventionally using X-rays on the right, 12(*a*) and (*b*) show a sigmoid loop, 12(*c*) and (*d*) show an alpha loop, and 12(*e*) and (*f*) show a reverse alpha loop.

FIG. 8 depicts schematically the three spheres of constant induced voltage when the errors in R have been reduced to allow the location of the sensor to be determined uniquely. The technique employed thus guarantees convergence to a unique location, with a precision that can be chosen in accordance with the requirements of the application. Indeed, it should be noted that in applications where the sensor is moving within the magnetic field, the number of iterations can be chosen dynamically for each calculation of the location of the sensor, thereby improving the efficiency of the process. For example, the first placement of the sensor typically requires 10 iterations before the solution is considered to have converged: this is considered to be so when the mean-square difference between the present and previous values of $\alpha$ is less than $10^{-6}$. Even with rapid movements of the sensor, it is unlikely that its angle $\alpha$ will change markedly from one positional placement to the next. By using the final value of $\alpha$ arrived at during the first placement as the initial estimate in the second placement, the number of iterations required to achieve the same convergence is significantly reduced. And so on for all subsequent placements. Experiments have shown that as few as 3–5 iterations are required for convergence after the initial placement.

Although the algorithm described above with reference to FIG. 7 ensures convergence to a unique location, allows both the location and orientation of a single coil sensor to be determined, and has proved to be robust even in the presence of noisy signals from the sensor coil 7, a second, alternative algorithm has been developed which has further advantages.

The first algorithm requires, at step 5, the solution of nine simultaneous equations relating $\theta$ and $\phi$ for each of the field generators to the estimate of the x, y and z coordinates of the sensor. This calculation can, dependent on the processing power of the controller 6, be time consuming, hence a second algorithm which is less computationally intensive has been developed. This algorithm enables the location and orientation of the sensor 7 to be determined more rapidly. The second algorithm is based on the realisation that mathematically the voltages induced in the sensor 7 by each set of three generating coils 3 comprising each generator can be treated as vector quantities. This mathematical treatment enables an angle $\psi$ between the magnetic field lines and the direction vector of the sensor from a generator to be calculated. Once the values of $\psi$ for each Generator have been found there is no need to employ equation (4) since the values of $\alpha$ can be calculated directly from the values of $\psi$ given a knowledge of the form of the magnetic field. Since nine versions of equation (4) need no longer be solved this algorithm is computationally less intensive than the algorithm of FIG. 7.

Figure 9:
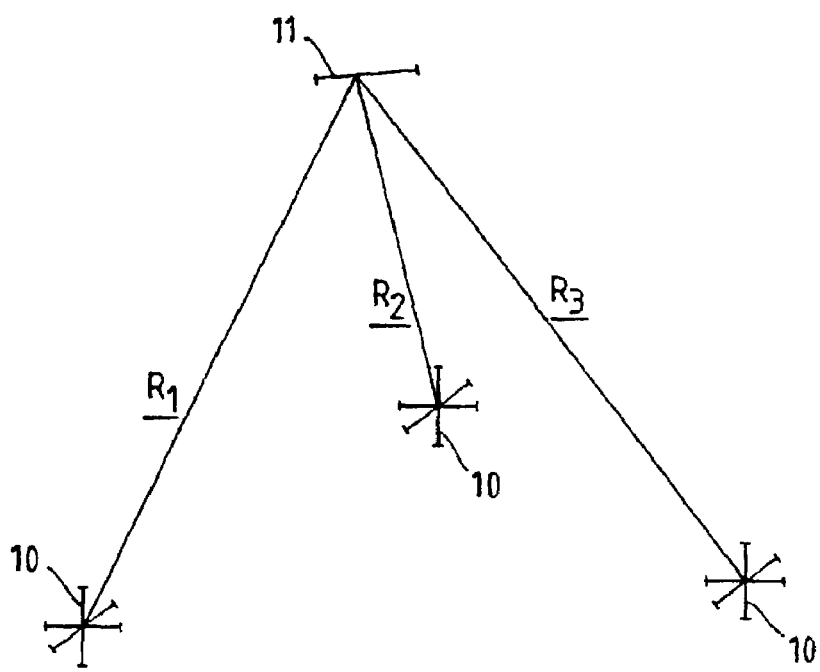

The second algorithm will now be described in greater detail. In order to explain the algorithm clearly and to demonstrate the mathematical insight on which it is based, the roles of the generating coils 3 and sensor coil 7 will be reversed i.e. for the purpose of the calculation the single axis field sensor 7 will be replaced by a continuously energised single axis field generating coil and the three orthogonal three-axis field generators will be replaced by three orthogonal three-axis field sensors. This is shown in FIG. 9. Although it should be stressed that the reversal of roles here is simply for the purpose of mathematical elegance, this reversed configuration will in practice be feasible and in some position location applications may be desirable.

Figure 10:
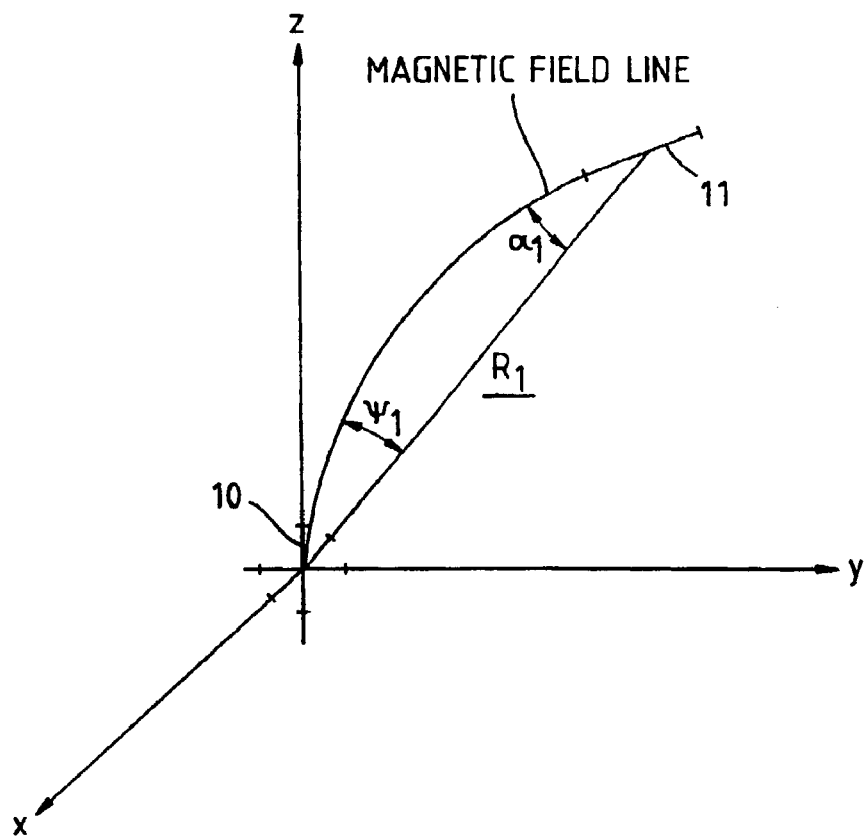

Referring now to FIG. 9, let the vectors joining each three-axis sensor (10) to the single axis generator (11) be $R_1$, $R_2$ and $R_3$ and let the angles between these vectors and the generator be $\alpha_1$, $\alpha_2$ and $\alpha_3$. The field produced by the single axis generator (11) will pass through each three-axis sensor (10), and the magnitude and direction of the field may be determined by processing the signals produced by each of the three orthogonal sensor coils (12), forming each three-axis sensor (10), in response to the field. Let the signals in each of the three-axis sensor (10) be represented by the vector quantities $V_1$, $V_2$ and $V_3$, where each component of the vectors corresponds to the signal in each of the orthogonal sensing coils (12). Let the angle between the field at each three-axis sensor (10) and the vectors $R_1$, $R_2$ and $R_3$ be $\psi_1$, $\psi_2$ and $\psi_3$ respectively, as shown in FIG. 10.

For the first estimate of the position of the generator 11, the orientation of the generator (11) is unknown, and $\alpha_1$, $\alpha_2$ and $\alpha_3$ are assumed to be zero. The magnitude of the vectors $R_1$, and $R_2$ and $R_3$ are then calculated from equation (11). As for the first algorithm, because of the nature of equation (11) a bounded value for the distance of the generator (11) from each of the three-axis sensors (10) is found and the overlap of these bounded values can be used to give an initial estimate of the x, y and z components of each of the vectors $R_1$, $R_2$ and $R_3$.

The angles $\psi_1$, $\psi_2$ and $\psi_3$ are then calculated using the dot product, as follows:

$$V_n \cdot R_n = |V_n||R_n| \cos \psi_n$$

$$\cos \psi_n = \frac{V_n \cdot R_n}{|V_n||R_n|}$$

Figure 11:
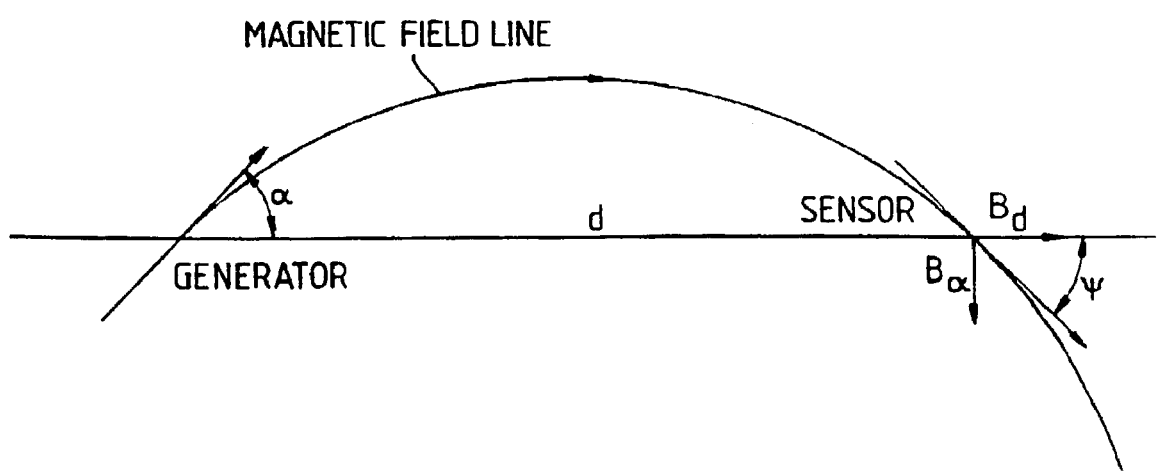

Having found $\psi_n$, we need to find $\alpha_n$ to improve the estimate of position. Referring to FIG. 11 $\psi$ is the known angle and $\alpha$ is the required angle. d represents the calculated distance from the generator to the sensor.

Since the generator is a simple dipole, the field at the sensor is given from equations (A-1) and (A-2) of the Appendix by:

$$B_d = \left(\frac{2k}{d^3}\right)\cos\alpha$$

$$B_a = \left(\frac{k}{d^3}\right)\sin\alpha$$

The angle of the field at the sensor is given by:

$$\tan\psi = \frac{-B_a}{B_d} = -\frac{1}{2}\tan\alpha$$

and so $\alpha$ is obtained from $\psi$ using:

$$\tan \alpha_n = -2 \tan \psi_n$$

Having found a new estimate for $\alpha_n$, a new estimate of the generator position is calculated using equation (11). The process is repeated until the position converges to the required degree of accuracy.

Once the position of the generator (11) has been determined in terms of $R_n$ and $\alpha_n$ the orientation of the generator may be calculated in terms of $\theta$ and $\phi$ as follows.

Let U be a unit vector defining the orientation of the generator relative to the sensors. Using the dot product, we can set up three equations to determine the three unknowns in U.

$$R_1 \cdot U = |R_1||U| \cos \alpha_1 = |R_1| \cos \alpha_1$$

$$R_1 \cdot U = |R_2||U| \cos \alpha_2 = |R_2| \cos \alpha_2$$

$$R_1 \cdot U = |R_3||U| \cos \alpha_3 = |R_3| \cos \alpha_3$$

These linear equations are solved to find U, and then the orientation in terms of θ and φ is given by:

$$\theta = \arctan\left(\frac{\sqrt{U_x^2 + U_y^2}}{U_z}\right)$$

$$\phi = \arctan\left(\frac{U_x}{U_y}\right)$$

(note that a four quadrant arctan function should be used).

Although the formulation of the second algorithm has thus far been for the case of a single axis generator and multiple axis sensors the algorithm can be applied to the case of a single axis sensor and multiple axis generators. The only modification required between the two cases is the method by which the raw data for the algorithm (i.e. the voltages induced) is acquired. The equations developed above are directly applicable to the single axis sensor multiple axis generator case since the magnetic coupling between two coils is the same irrespective of which of the two coils is being driven.

The steps to be followed when employing the algorithm for the single axis sensor and multiple axis generator case will now be summarised:—
1. Sequentially energise each of the three generator coils in each of the three generators 1 and measure the voltage induced in the sensor coil 7 by each generator coil i.e. measure $V_{1x}$, $V_{1y}$, $V_{1z}$, $V_{2x}$, $V_{2y}$, $V_{2z}$, $V_{3x}$, $V_{3y}$, $V_{3z}$.
2. Invoke $\alpha_n$ in equation (11) and compute $|R_n|$ for each of the generator 1, 2 and 3. (for initial estimate set α=0).
3. From the intersection of three spheres of radius $|R_n|$ calculate the vector quantities $R_1$, $R_2$ and $R_3$.
4. Taking the three voltages induced in the sensor coil 7 by a single generator 1 as a vector quantity e.g.

$$V_1 = V_{1x}x + V_{1y}y + V_{1z}z$$

calculate the angle of the field $\psi_n$ from the dot product $V_n \cdot R_n$.
5. Calculate the angles $\alpha_n$ between the vectors $R_n$ and the sensor axis from $\psi_n$ and equations A-1 and A-2.
6. Repeat steps 2 to 5 until the desired level of positioning accuracy has been achieved.
7. Use final values of $\alpha_n$ and $R_n$ to calculate the orientation of the sensor coil in terms of θ and φ.

It has been found that use of the second algorithm can improve the speed with which the location and orientation of a sensor is determined by a factor of approximately 15 compared to the first algorithm.

For both algorithms the location and orientation of more than one sensor can be determined without the need to replicate the field generators 1 and amplifier 5. The field generated by any one field generating coil is measured at each of the sensors and the location and orientation of the sensors are simultaneous and independently calculated. The positions of the sensors may of course all be displayed on a single display unit 9.

The simple, small sensor used in this embodiment means that it can provide position location in many situations where there is insufficient space for the three coil orthogonal sensor used in prior art position location systems. A particular field of application is the medical field, where access through body vessels is required, for example in endoscopy or non-invasive cardiovascular heart surgery. In these medical situations the present location system may replace the use of x-ray imaging (fluoroscopy, e.g. using an x-ray imaging system, for example a C-arm 100 such as those generally known in the art (FIG. 1)), giving considerable advantages in cost and eliminating x-ray exposure to both patients and medical staff. The low frequency magnetic fields used by the present system render the human body transparent, while the use of low field strengths ensures the system is intrinsically safe.

During endoscopy it is desirable to know the path of the endoscope through the body. This may be achieved using the present location system in three ways. Firstly, the single sensing coil may be pulled along the biopsy tube and its position at regular intervals along the tube stored and displayed to provide a 3D map of the path. Secondly, a tube containing approximately a dozen single coil sensors may be placed in the biopsy tube of the endoscope and the location of each of the sensors determined. This would be a retro-fit to existing endoscopes. Alternatively, the single coil sensors may be placed in the wall of the endoscope during manufacture in the second two cases a real time picture of the path of the endoscope would be available at all times to the endoscopist.

The present positioning system has been utilised in clinic field trials to image in three dimensions the total configuration of a colonoscope within the human abdomen. A sensor according to the present invention was placed inside the biopsy channel of an endoscope.

The small inner diameter of the biopsy channel, typically 3.7 mm for a colonoscope, not only dictates that the sensor be of vanishingly small diameter, but also that it may only comprise a single coil, typically 1 cm in length, orientated along the axis of the instrument. The algorithms of the present positioning system processes the signals from this sensor in such a way as to calculate the position of the sensor within the biopsy channel independent of its orientation. Such independence is crucial in colonoscopy since the sensor may adopt any orientation for a single x-y-z location.

The positioning algorithm resides as software within an IBM 486 personal computer which, upon processing the information taken from the sensor at numerous discrete positions along the biopsy channel, then displays the path followed by the sensor as a continuous line on the monitor. Clearly this path corresponds precisely to that of the endoscope. Moreover, because the information from the sensor at each location relates to three dimensions, the imaged path on the monitor is likewise displayed in three dimensions. Visually the system achieves this by the use of "grey scale" colour coding whereby portions of the path further from the viewer (i.e. down into the screen) appear in darker shades of grey than the "under" portion. This feature is unique among all conventional imaging techniques for colonoscopy and represents a major advance in the field.

To display the path of the endoscope, the endoscopist first passes the sensor down he biopsy channel until it reaches the tip of the endoscope. For convenience we have encapsulated the sensor within a hollow tubular catheter of the type used routinely with endoscopes The catheter is then withdrawn at a uniform speed (although this is not critical) while the system repeatedly determines the position of the sensor at discrete instances during its motion. During withdrawal the path of the instrument is displayed on the monitor in three dimensions. In many situations a total image of the endoscope is not required, in which case the sensor need only be withdrawn along that portion of the instrument of interest. To cater for patients lying in a variety of positions, perhaps changing during the investigation, the image may be rotated in any direction. This is particularly advantageous in establishing the radius of curvature of any bend in the endoscope that happens to lie along the viewing axis. For example, a bend that is in fact gradual, and hence poses no concern, can appear abrupt if viewed from some directions. A useful zoom facility on the image is also provided. When the system is in normal use, the system display would ideally be sited next to a standard camera monitor used to display the view from the endoscope. In this way the endoscopist is conveniently presented with the path of the instrument in three dimensions on one display, and the internal view from the endoscope optics on the other.

Figure 12:
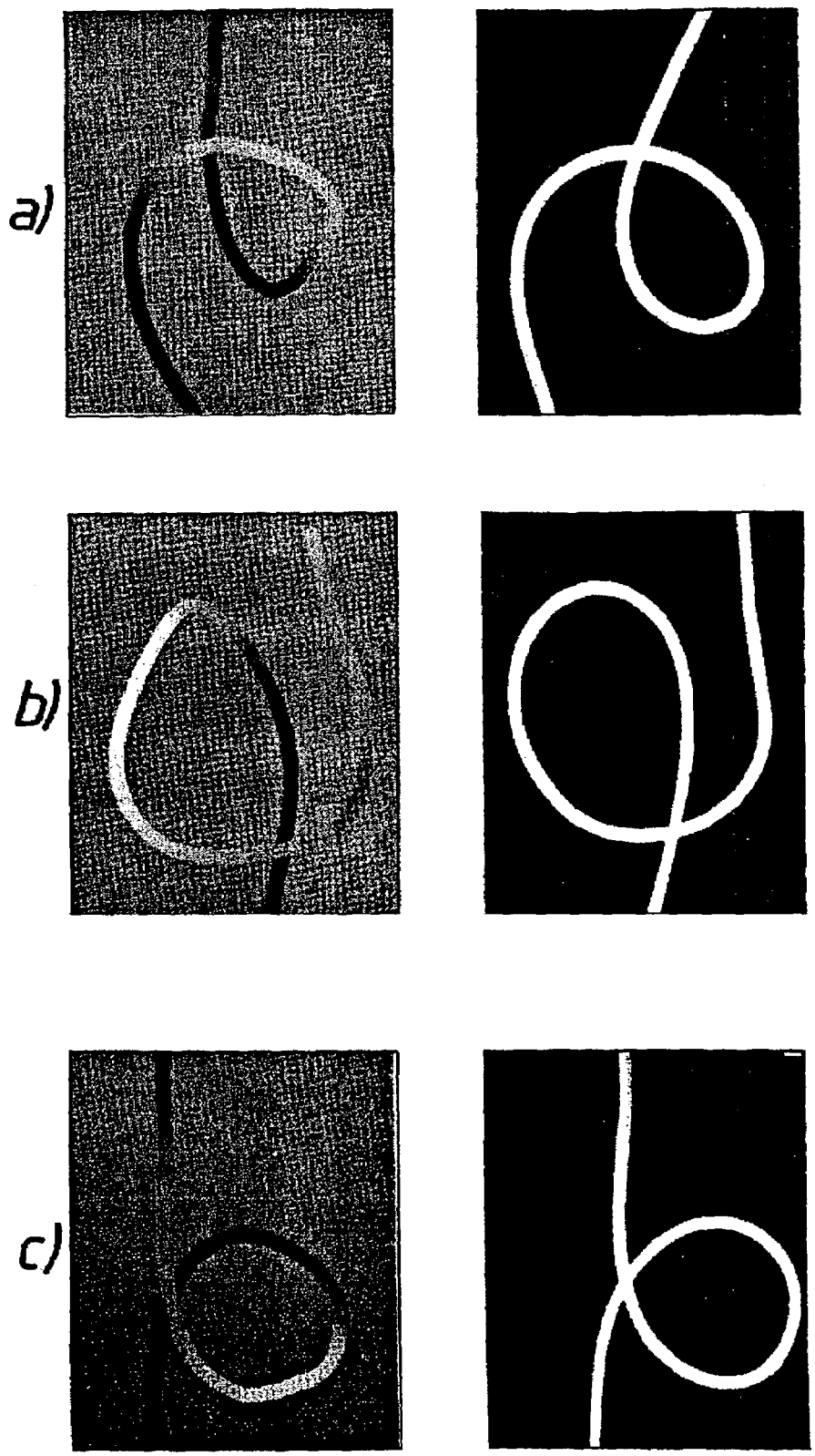

Initial validation of the system was performed with the aid of a rigid plastic framework to hold the endoscope in one of a number of predefined configurations. X-ray imaging and the present magnetic field system were applied to seven different configurations of the endoscope. These included a sigmoid loop, an alpha loop, a reverse alpha loop, a gamma loop, and an "N" loop. The results, three of which can be seen in FIG. 12 showed close agreement between the image produced by the present positioning system (shown on the left) and the X-ray image (shown on the right) in each case. The nature of the overlapping portions of the colonoscope can be clearly seen from the images produced by the present positioning system. Some distortion of the images was caused by the metallic construction of the colonoscope perturbing the magnetic fields. However, this was minimal and the colonoscope configuration is clearly evident from the images.

The clinical trails involved three patients undergoing colonoscopy for a number of different indications. Ethical approval was obtained, as was written consent. The patients were sedated with a combination of pethidine and midazolam before the examination. The colonoscope used was a Pentax type FC38LH.

Figure 13:
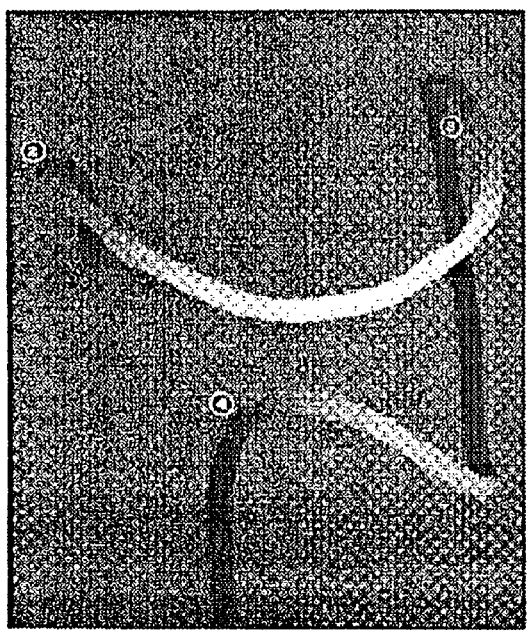
FIG. 13 shows images of an endoscope within a patient obtained using the present positioning system on the left, and obtained using conventional X-ray imaging on the right, 13(*c*) and (*d*) show a lateral view.
Figure 13:
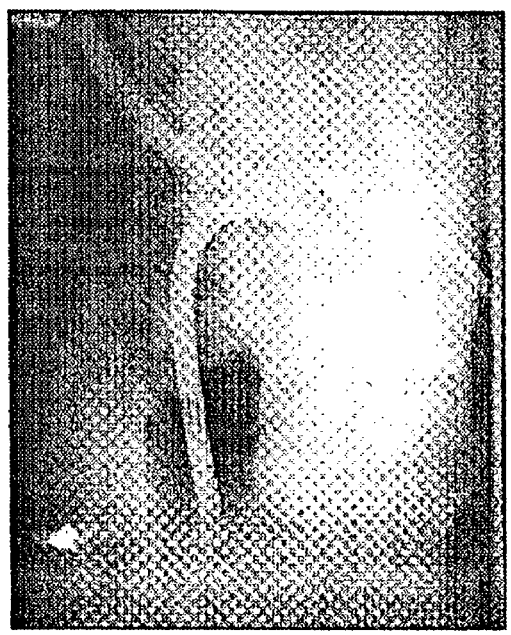
Figure 13:
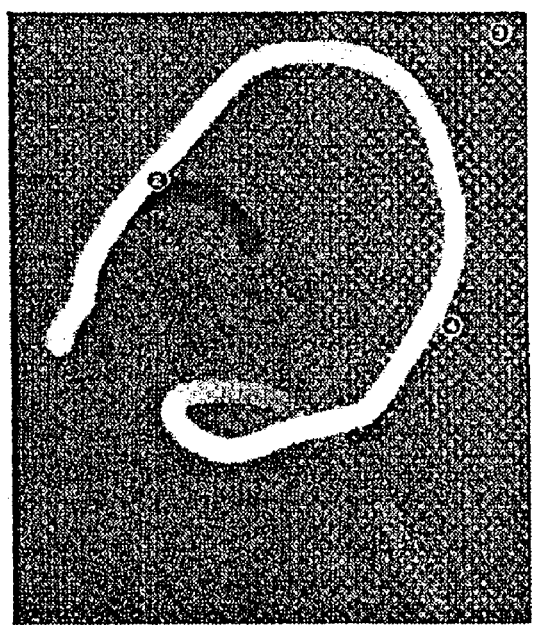
Figure 13:

For the majority of each examination, the sensor was fully inserted into the biopsy channel, and the display was configured to show the progress of the tip of the endoscope in real time. When progress became difficult, the sensor was withdrawn, which immediately produced an image on the screen of the total path of the endoscope. With the aid of this image the removal of loops was straightforward, by using clockwise or anti-clockwise twist and simultaneous withdrawal of the endoscope. Similarly, when re-inserting the instrument the reformation of loops was prevented by a combination of abdominal pressure and torque. Where abdominal pressure was required the sensor was positioned in the loop, so enabling the endoscopist to see, by referring to the displayed image, whether pressure was being applied in the desired direction and to the correct extent. In each case examination around to the caecum was achieved (i.e. total colonoscopy) and the procedure was tolerated well by the patients. During the examinations, X-ray pictures were taken for comparison against those obtained with the magnetic system. Two of these, a plan and side view, are shown in FIG. 13 together with the corresponding image from the magnetic system. Agreement between the two is very close, the deviation being largely attributable to patient movement between the two exposures.

The system has been shown to image the configuration of the endoscope within the patients's abdomen with close agreement to the X-ray image. The three dimensionality of the image has proven to be of great help in deciding the strategy for removing loops which form in the path of the endoscope during intubation. Indeed, this improvement in visualisation is likely to be of great benefit in teaching colonoscopy, as well as enabling experienced endoscopists to improve their technique when facing difficult cases. The intrinsically safe nature of the system allows it to be in continuous use throughout the examination, presenting the endoscopist with as many images as the circumstances require. This contrasts markedly with fluoroscopy which can only offer images intermittently and carries an exposure time limit for reasons of patient safety, and X-ray pictures which are essentially only a "one-shot" option. Moreover, protective clothing need not be worn by any of those present at the examination while the system is in use, nor is it necessary for the examination room to be in any way specially prepared. Indeed, the system frees such examinations from having to take place in a room apart from the ward. If need be such examinations could be carried out in complete safety and with no loss in overall integrity, at the patient's own bed in the ward.

A number of medical studies have considered the efficacy of colonoscopy as a screening methodology in asymptomatic subjects and have shown a significant detection rate for adenomas and carcinoma in subjects over the age of 60. Of particular note here is that some 50% of lesions were proximal to the splenic flexure, hence the importance of performing a total colonoscopy in such cases. The ability to conduct total colonoscopes routinely and efficiently is therefore an important objective. On the other hand it must be remembered that colonoscopy (total or otherwise) is associated with a certain morbidity and mortality due to the need to apply mechanical stress during intubation or withdrawal. The overall improvement in visualisation that the present system affords, particularly it's three dimensionality, should both raise the efficacy of total colonoscopy and reduce the risk of perforation. This in turn may also help to reduce the dosage of analgesic and sedative drugs required.

Although the application of the present positioning system to colonoscopy has been specifically addressed, the scope of the medical applications extends far beyond this by virtue of the very small size of the sensor(s). For example, bronchoscopy, gastroscopy and Procedures involving a nasogastric or endotracheal tube could all utilise the sensor described herein its present catheter form. Numerous other medical applications requiring position or orientation information could benefit from either a single or multiple sensor implementation of the system.

Data gloves which facilitate the location of a wearer's hands, are used in both medical and virtual reality applications. They enable the position and direction of each of the fingers to be determined. The prior art magnetic field location system using a three coil orthogonal sensor is clearly not applicable, so current data gloves use fibre optic strain gauges. These require calibration every 2–3 minutes. The ability to locate single coil sensors means that the sensors may be wound around each joint of each finger giving a system which is less bulky, more accurate and only requires calibration during the manufacture of the gloves.

Figure 15:
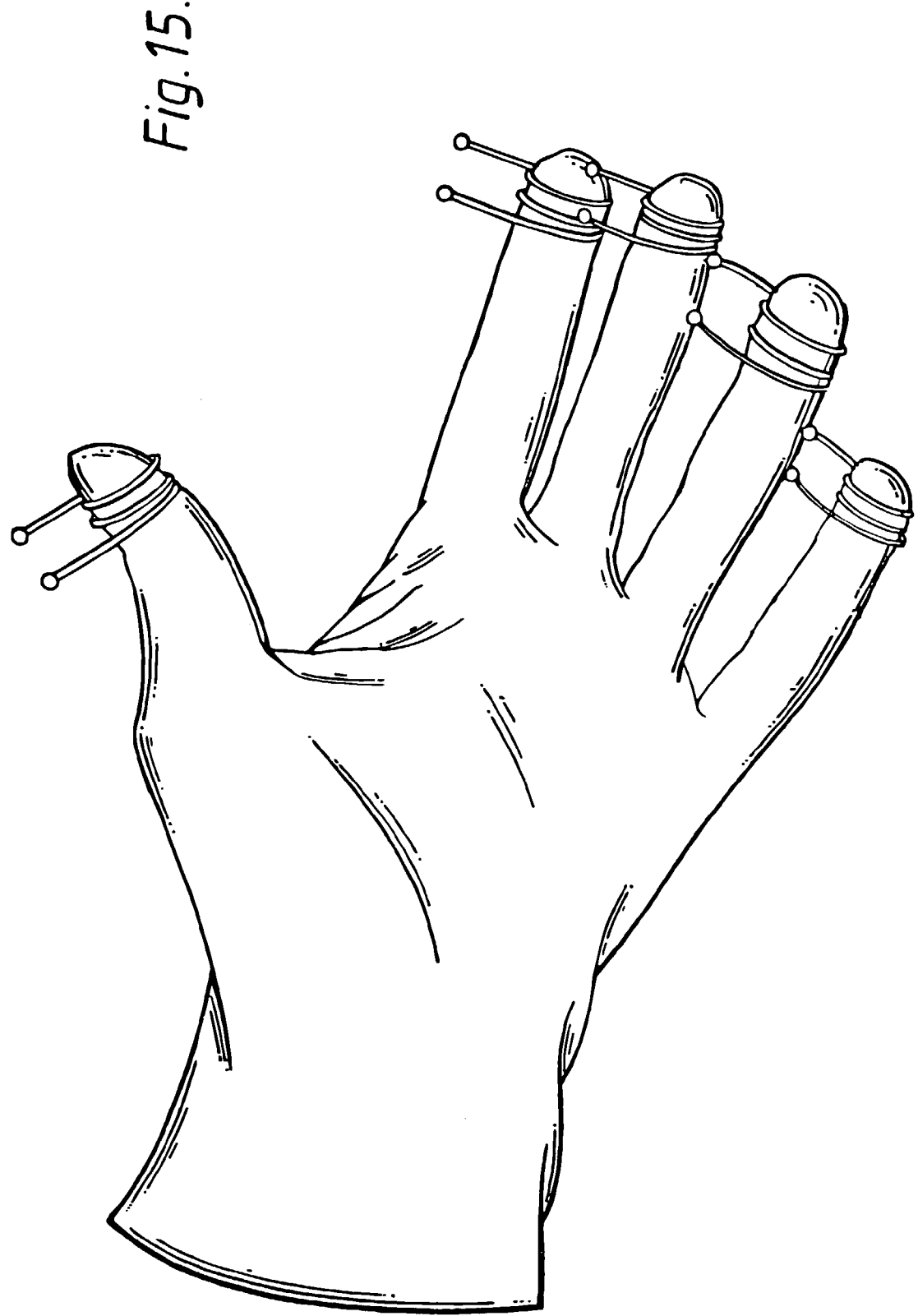
FIG. 15 is an illustration of a data glove having one or more sensor coils attached to fingers of the glove.
Figure 16:
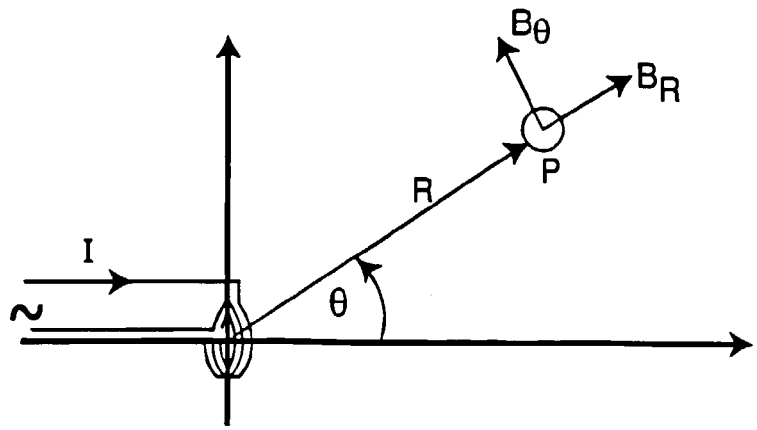
FIG. 16 depicts resolving magnetic flux density at a distance.
Figure 17:
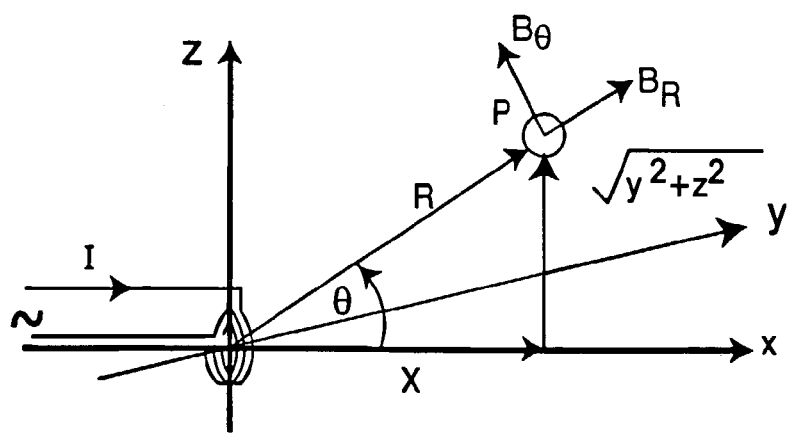
FIG. 17 depicts resolving magnetic flux density onto an x-y-z Cartesian coordinate system.
Figure 18:
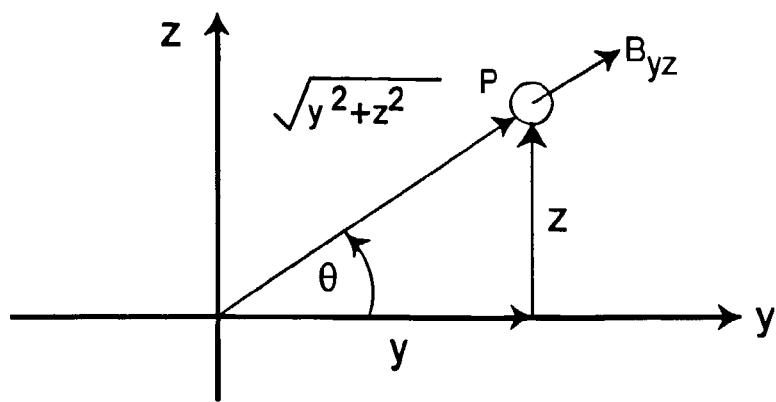
FIG. 18 depicts resolving the magnetic flux density at P on to the x-y plane and In a first embodiment the invention enables a sensor comprising a single sensing coil to be located in three dimensions relative to a plane defined by three field generators.

FIG. 15 illustrates an exemplary data glove with sensor coils wound around each finger.

A particular area of application for the present positioning system comprises that of the so called "man-machine interface". There are numerous situations in which a human operator needs to interact with a machine, or computer, normally comprising some form of display device, examples of such interactions are with a conventional personal computer, a video conferencing system, or a virtual reality environment in which the operators field of view is filled by the display device, which in this case may be three dimensional. The present positioning system allows an operator to wear small, single coil sensors about his body to enable his movements to be detected and interpreted by a machine without the need for physical contact between the operator and the machine. For example the positioning system of the present invention could enable an operator to interact with images on a television or computer screen without the use of a conventional keyboard, mouse or stylus. The operator could wear single coil sensors on his fingertips, for example in thimbles, or a thin glove, the location and orientation of which could be detected within a magnetic field generated within the vicinity of the display screen. Linking the positioning system to the computing system would allow the computing system to have knowledge of the position of the operators fingertips in three dimensions. A computer drawn replica of the user's hand which precisely emulates the movements of the user's own fingers, could then be utilised by the user to interact with the computer system. Thus when the user makes hand movements the virtual hand on the screen can be made to grasp and manipulate objects in the display, for example moving portions of text, rotating an engineering drawing, selecting an icon to activate a software program, etc. The virtual hand could also be used to control windows and menus and to draw diagrams. The advantage of such a man machine interface is that its use is completely intuitive, requiring no training.

Since the positioning system of the present invention enables the position of a sensor to be located in three dimensions, the extension of such a man machine interface to a three dimensional virtual reality environment is clearly possible. In this case the computer system involved may need information regarding the position of other parts of the operator's body than his hands, for example the image displayed to the operator may be dependent on the location and orientation of his head, in which case small single coil sensors can clearly be worn for example on each temple.

In a second embodiment the invention enables a sensor, comprising three orthogonal sensing coils, to be located in three dimensions relative to a single field generator comprising three orthogonal generating coils.

With reference Go FIG. 9, a field generator 1, comprising three generating coils 3, as previously described is mounted on a surface 2. Each generating coil is electrically connected to an amplifier 5 and is driven as previously described.

The sensor 7 in this embodiment comprises three mutually orthogonal sensing coils, A, B and C, each of which is separately electrically connected to a measurement unit 8.

In use the three generating coils are sequentially energised as previously described, but when each coil is energised the voltages Induced in each of the three sensing coils $V_A$, $V_B$ and $V_C$ are measured by the measurement unit 8 and stored by the controller 6. The controller 6 then calculates from these three voltages the location of the sensor 7 relative to the single field generator 1.

The controller is able to calculate the location of the sensor, even though the axes of the generated fields have not been directed towards the sensor, by employing an algorithm which weights the voltages induced in the three sensing coils by a direction dependent weighting, and then alters these weightings to achieve a calculated maximum field strength at the sensor. In order to more fully describe this algorithm the field from a single small coil is first considered.

The magnetic field produced by a small coil, from equations (A-1) and (A-2), is given by:

$$B = \left(\frac{k}{R^3}\right)(2a_r\cos\theta + a_\theta\sin\theta) \quad (12)$$

where R=distance from the coil
θ=angle from the axis of the coil
k=constant for coil (size, drive current, no. turns etc).
$a_R$ is a unit vector in the direction of $B_R$ (see Appendix A—FIG. A-1)
$a_\theta$ is a unit vector in the direction $B_\theta$ (see Appendix A—FIG. A-1).

Now, the magnitude of the magnetic field $$|B| = \frac{k}{R^3}\sqrt{3\cos^2\theta + 1} \quad (13)$$

and so it can be seen that for a given distance from the coil, the field strength is greatest when θ=0 i.e. on the axis of the coil. Clearly, if the effective axis of the coil could be directed towards the sensor, the sensor would experience a maximum in field strength.

In order to steer the effective axis of the coil without physically moving it, additional coils are required. To steer the effective axis over 3D, three coils are required in total. Assuming three mutually perpendicular coils $D_x$, $D_y$, $D_z$ lying along each of the cartesian axes x, y and z, each coil being centred on the origin, by setting the currents to each coil as:

$I_x$=I cos θ cos φ
$I_y$=I cos θ sin φ
$I_z$=I sin θ the effective axis of the resulting field may be steered without changing the magnitude of the field. φ is the angle anticlockwise from x in the xy plane, and θ is the elevation towards the z axis.

Assuming the notation of FIG. 2, OP represents the effective axis of the field. That is a single drive coil, centred on the origin, with its axis along OP, fed with current I, would create the same field as the three coil arrangement with the currents $I_x$, $I_y$, and $I_z$ as described.

Thus if the field strength at the point we wished to locate could be measured, we would find that when axis OP pointed at this point, the field strength would be a maximum.

The field strength is measured using 3 orthogonal sense coils, centred on a single point. In this case an AC field must be used in the drive coils. Let the sensor coils be A, B and C, and let the amplitude of the voltages induced by $V_A$, $V_B$ and $V_C$. The field strength can be computed from $$B = k_s(V^2_A + V^2_B + V^2_C)^{1/2}$$

where $k_s$=a constant for the sensor and frequency used.

The effective axis of the resulting field, could be physically steered towards the sensor, and $V_A$, $V_B$, $V_C$ monitored to maximise B. However this is difficult in practice to achieve since both θ and φ would need to be simultaneously altered while measurements from the sensor are taken. This leads to slow position location, and limits the system to locating a single sensor. The approach adopted in this embodiment is as follows. The drive currents for all the coils are set to I, and not to the values which would be required to physically steer the effective field axis, as discussed above.

i.e. $I_x$=I
$I_y$=I
$I_z$=I

Effectively steering of the field axis is carried out AFTER the field measurements have been made by weighting or scaling these measurements by direction dependent weighting factors. Thus, instead of physically altering θ, φ and then measuring B, the following technique is used.
1. Switch on $D_x$, with $I_x=I$
2. Measure $V_{ADx}$, $V_{BDx}$, $V_{CDx}$
3. Switch off $D_x$; Switch on $D_y$, with $I_y=I$
4. Measure $V_{ADy}$, $V_{BDy}$, $V_{CDy}$
5. Switch off $D_y$; Switch on $D_z$, with $I_z=I$
6. Measure $V_{ADz}$, $V_{BDz}$, $V_{CDz}$
7. Switch off $D_z$ For the physically steered field: $I_x=I \cos\theta \cos\phi$, rather than I. The same result is achieved by weighting the results from step 3 by $\cos\theta \cos\phi$. The same logic applies to the remaining results, using the relevant weighting factor.

Thus:

$$B^2 = K_s^2((V_{ADx}\cos\phi + V_{ADy}\sin\phi)\cos\theta - V_{ADz}\sin\theta)^2 + \\ ((V_{BDx}\cos\phi + V_{BDy}\sin\phi)\cos\theta + V_{BDz}\sin\theta)^2 + \\ ((V_{CDx}\cos\phi + V_{CDy}\sin\phi)\cos\theta + V_{CDz}\sin\phi)^2$$

Note that the "signs" of the amplitude are important
phase shift =O=+ve
phase shift=π=−ve In this expression for $B^2$, θ and φ are the only variables.

In order to find the values of θ and φ which give the maximum $B^2$, she Gauss-Newton optimisation technique is used. This copes well with sum of squares type expressions. The expression for $B^2$ is well behaved, and only a few iterations are required.

In order to find the precise location of the sensor we must now find R.

If we square and sum the field magnitudes at the sensor for each generator coil, we find that:

$$|\underline{B}_{0x}|^2 + |\underline{B}_{0y}|^2 + |\underline{B}_{0z}|^2 = 6\left(\frac{k_c}{R^3}\right)^2$$

and so R may be found from:

$$R^3 = k_c\sqrt{\frac{6}{|\underline{B}_{0x}|^2 + |\underline{B}_{0y}|^2 + |\underline{B}_{0z}|^2}}$$

The cartesian coordinates of the sensor are then
x=R cos θ cos φ
y=R cos θ sin φ
z=R sin θ

As with the first embodiment the location of multiple sensors is facilitated because the generating coils are only energised sequentially allowing the generated field to be simultaneous measured at any number of locations.

Although in both embodiments of the invention described herein the voltages induced in the sensor coil 7 by the generating coils 3 are distinguished one from the other by employing a time multiplexing approach, i.e. the generating coils are energised sequentially, a frequency multiplexing approach may also be adopted within the scope of the present invention. For example in such an approach each generator coil 3 could be driven at a different frequency so that a plurality of generating coils 3 could be simultaneously energised while still allowing the voltage induced in the sensor 7 by each generating coil to be distinguished by its frequency. In such an arrangement the sensor would need to be responsive to all the energising frequencies and some form or frequency filtering would need to be provided. This filtering could be provided by discrete physical bandpass filters electrically connected to the sensor 7, or, if an A to D converter is employed as described herein, filtering of the signal from the sensor 7 can be accomplished by signal processing software in the controller 6. The use of frequency multiplexing to acquire the data for position determination can significantly increase the operating speed of the positioning system since measurements from generating coils can be taken simultaneously. Disadvantages of such a frequency multiplexing system are that it is more complex than a time multiplexed system and requires greater electrical bandwidth. A combination of time and frequency multiplexing could of course be used.

In both embodiments it is desirable that the quasi-static magnetic field generated by a coil is established quickly and is allowed to decay quickly. For this reason it is preferred to use a first order rather than a second order drive circuit. For the generating coils employed the field settles within one cycle of being switched on.

It will be appreciated that alternative configurations of both embodiments for different applications, for example locating a sensor within a two dimensional plane, are envisaged within the scope of the present invention.

As will be clear to one skilled in this art, the roles of the generating and sensing coils may be reversed while still benefitting from the advantages of the present invention. That is the sensing coil or coils may be used as field generating elements, and the generating coils may be used as field sensing elements.

This reversal of roles has particular advantage where a static field, such as that generated by a bar magnet is employed according to the first aspect of the invention, since such a field generating element must be effectively permanently "energised". The reversal of roles allows the "sensor" permanently to generate a field which is sensed at each of the "generating elements" and the location and orientation of the "sensor" is then determined as before.

Appendix A

Consider a current, I, flowing through a small planar coil of radius, b, (Fig A-1). The frequency of I is chosen to be sufficiently low such that static field distributions apply.

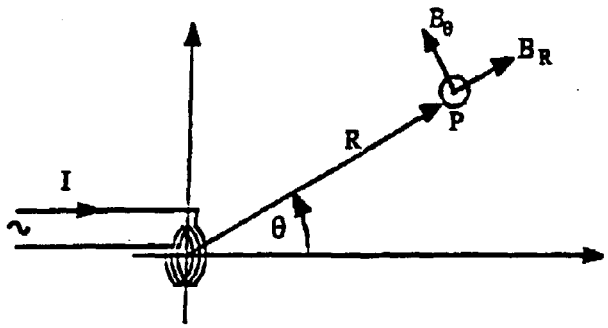

Fig A-1. Resolving magnetic flux density at a distance.

For a point P in the field whose distance R from the coil is such that R>>b, it is readily shown for example in D K Cheng, Field and Wave Electromagnetics, 2nd Ed, Addison Wesley, 1989, that $$B_R = \frac{2 k_c \cos \theta}{R^3} \quad \text{......(A-1)}$$

and, $$B_\theta = \frac{k_c \sin \theta}{R^3} \quad \text{......(A-2)}$$

where $k_c$ is a known function of I and b. $B_R$ and $B_\theta$ represent the vector components of the magnetic flux density at point P resolved along axes parallel to the line R and the angle $\theta$. Note that, by convention, $\theta$ is measured from the axis of the coil.

In order to resolve the magnetic flux density at P onto a 3-dimensional cartesian coordinate system, consider first the coil in the y-z plane, centred on the origin (Fig A-2).

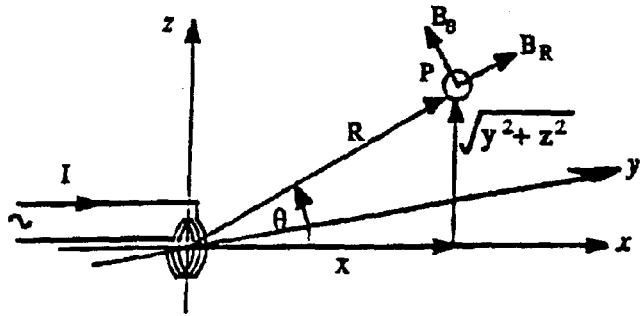

Fig A-2. Resolving magnetic flux density onto an x-y-z cartesian coordinate system.

If point P is distance x from the coil (i.e. origin) along the x-axis, and its vector distance is R, the distance in the y-z plane by Pythagoras is $\sqrt{R^2 - x^2}$. Since $R^2 = x^2 + y^2 + z^2$, this distance reduces to $\sqrt{y^2 + z^2}$, as shown. It then follows that, $$\sin\theta = \frac{\sqrt{y^2 + z^2}}{R} \qquad \ldots(A-3)$$

and, $$\cos\theta = \frac{x}{R} \qquad \ldots(A-4)$$

Resolving the magnetic flux density at P onto a cartesian system gives, for the x-axis component, $$B_x = B_R \cos\theta - B_\theta \sin\theta$$

From (A-1) and (A-2) this becomes, $$B_x = \frac{k_c}{R^3}\left(2\cos^2\theta - \sin^2\theta\right)$$

and from (A-3) and (A-4), $$B_x = \frac{k_c}{R^5}\left(2x^2 - y^2 - z^2\right) \qquad \ldots(A-5)$$

Resolving similarly onto the y-z plane gives, $$B_{yz} = B_R \sin\phi + B_\theta \cos\phi$$

which from (A-1) and (A-2) becomes, $$B_{yz} = \frac{k_c}{R^3}\left(3\cos\theta\sin\theta\right)$$

and from (A-3) and (A-4), $$B_{yz} = \frac{k_c}{R^5}\left(3x\sqrt{y^2 + z^2}\right) \qquad \ldots(A-6)$$

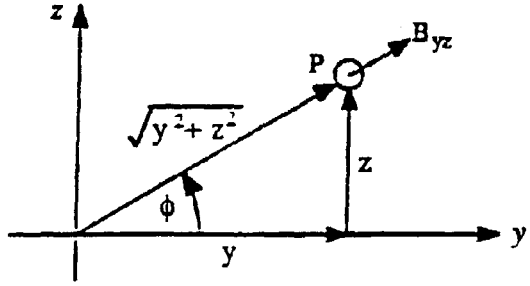

Fig A-3. Resolving the magnetic flux density at P onto the y-z plane.

Resolving the magnetic flux density at P into its y and z components (Fig A-3) gives, $$B_y = B_{yz}\cos\phi = B_{yz}\left(\frac{y}{\sqrt{y^2 + z^2}}\right)$$

and,
$$B_z = B_{yz} \sin \phi = B_{yz}\left(\frac{z}{\sqrt{y^2+z^2}}\right)$$

From (A-6) these become, $$B_y = \frac{k_c}{R^5}(3xy) \quad\quad\quad \text{.....(A-7)}$$

and, $$B_z = \frac{k_c}{R^5}(3xz) \quad\quad\quad \text{.....(A-8)}$$

For a coil (dipole) in the y-z plane, equations (A-5), (A-7) and (A-8) fully describe the resolved cartesian components of the magnetic flux density at a point P located at a radial distance R from the coil. The corresponding equations for coils in the x-y and x-z planes can be developed in an identical manner. The complete set of formulae can therefore be summarised thus.

*For a coil in the y-z plane :-*

$$B_x = \frac{k_c}{R^5}(2x^2 - y^2 - z^2) \quad\quad\quad \text{.....(A-9)}$$

$$B_y = \frac{k_c}{R^5}(3xy) \quad\quad\quad \text{.....(A-10)}$$

$$B_z = \frac{k_c}{R^5}(3xz) \quad\quad\quad \text{.....(A-11)}$$

*For a coil in the x-y plane :-*

$$B_x = \frac{k_c}{R^5}(3xz) \quad\quad\quad \text{.....(A-12)}$$

$$B_y = \frac{k_c}{R^5}(3yz) \quad\quad\quad \text{.....(A-13)}$$

$$B_z = \frac{k_c}{R^5}(2z^2 - x^2 - y^2) \quad\quad\quad \text{.....(A-14)}$$

*For a coil in the x-z plane :-*

$$B_x = \frac{k_c}{R^5}(3xy) \quad\quad\quad \text{.....(A-15)}$$

$$B_y = \frac{k_c}{R^5}(2y^2 - x^2 - z^2) \quad\quad\quad \text{.....(A-16)}$$

$$B_z = \frac{k_c}{R^5}(3yz) \quad\quad\quad \text{.....(A-17)}$$

The invention claimed is:

1. A medical navigation apparatus for navigating an anatomical body during a medical procedure, the medical navigation apparatus comprising:
 a medical instrument operable to be navigated through the anatomical body during the medical procedure;
 at least one field sensor associated with the medical instrument and operable to be moved in association with the medical instrument;
 at least one magnetic field source operable to radiate at least one magnetic field into the anatomical body and operable to be detected by the at least one field sensor;
 a controller operable to receive from the at least one field sensor signals indicative of the at least one magnetic field and operable to continuously ascertain positions of the at least one field sensor based upon the at least one magnetic field detected by the at one least field sensor; and
 a display operable to continuously display representations of the position of the at least one field sensor associated with the medical instrument as it moves from a first position to a second position to form continuous representations, wherein the continuous representations include a representation of the first position, a representation of the second position, and representations of the positions between the first position and the second position
 wherein the continuous representations of the position of the at least one field sensor is operable to be rotated in any direction on the display to illustrate the continuous representations from a plurality of perspectives of the continuous representations.

2. The medical navigation apparatus as defined in claim 1 wherein the medical instrument is a catheter.

3. The medical navigation apparatus as defined in claim 1 wherein the medical instrument is an endoscope.

4. The medical navigation apparatus as defined in claim 1 wherein the medical instrument is a colonoscope.

5. The medical navigation apparatus defined in claim 1 wherein the medical instrument is used for a cardiac medical procedure.

6. The medical navigation apparatus as defined in claim 1 wherein the at least one field sensor includes a single sensing coil.

7. The medical navigation apparatus as defined in claim 6 wherein the single sensing coil is an air-core coil.

8. The medical navigation apparatus as defined in claim 6 wherein the single sensing coil includes a magnetic permeable core.

9. The medical navigation apparatus as defined in claim 1 wherein the at least one field sensor is a flux gate magnetometer.

10. The medical navigation apparatus as defined in claim 1 wherein the at least one field sensor includes three sensing coils oriented orthogonal to one another about a common origin.

11. The medical navigation apparatus as defined in claim 1 wherein the at least one magnetic field is a quasi-static magnetic field.

12. The medical navigation apparatus as defined in claim 1 wherein the medical procedure is selected from a group comprising a colonoscopy, a bronchoscopy, a gastroscopy, a nasogastric procedure, an endotracheal procedure, cardiovascular procedure, and a combination thereof.

13. The medical navigation apparatus as defined in claim 1 wherein the at least one magnetic field source includes a first magnetic field source operable to generate a first magnetic field, a second magnetic field source operable to generate a second magnetic field and a third magnetic field source operable to generate a third magnetic field.

14. The medical navigation apparatus as defined in claim 13 wherein the first, second, and third magnetic field sources are positioned at known locations in a two-dimensional plane.

15. The medical navigation apparatus as defined in claim 14 wherein the first, second, and third magnetic field sources each include three coils oriented orthogonal to one another about a common origin.

16. The medical navigation apparatus as defined in claim 13 wherein the first, second, and third magnetic fields are sequentially generated in a time multiplexed manner.

17. The medical navigation apparatus as defined in claim 13 wherein the first, second, and third magnetic fields are generated in a frequency division multiplexed manner.

18. The medical navigation apparatus as defined in claim 13 wherein the first, second, and third magnetic field sources have a same center location.

19. The medical navigation apparatus as defined in claim 13 wherein the first, second, and third magnetic field sources each have a unique center location different from the center location of the other two field sources.

20. The medical navigation apparatus as defined in claim 1 wherein the at least one magnetic field source includes one field coil.

21. The medical navigation apparatus as defined in claim 1 wherein the at least one magnetic field source includes three field coils oriented orthogonal to one another about a common origin.

22. The medical navigation apparatus as defined in claim 1 wherein the ascertained positions include both the location and orientation of the at least one field sensor associated with the medical instrument.

23. The medical navigation apparatus as defined in claim 1 wherein the display is further operable to simultaneously display local information corresponding to an area in the anatomical body where the at least one field sensor is located while displaying the representation of the ascertained position of the at least one field sensor.

24. The medical navigation apparatus as defined in claim 23 wherein the local information is an image.

25. The medical navigation apparatus as defined in claim 1 wherein the at least one magnetic field is a near-field electromagnetic field.

26. The medical navigation apparatus as defined in claim 1 wherein the controller is operable to calculate from the signals a location, an elevation angle and a rotation angle of the at least one field sensor.

27. The medical navigation apparatus as defined in claim 1 wherein continuously displaying representations further includes displaying a three-dimensional map formed based on the representations.

28. The medical navigation apparatus as defined in claim 27 wherein contours of the anatomical body are displayed as a three-dimensional map.

29. The medical navigation apparatus as defined in claim 27 wherein the display is operable to simultaneously display an actual image of an internal structure of the anatomical body with the three-dimensional map.

30. The medical navigation apparatus as defined in claim 1 wherein the at least one field sensor is attached to the medical instrument and moves with the medical instrument.

31. The medical navigation apparatus as defined in claim 1 wherein the at least one field sensor moves independent of the medical instrument.

32. The medical navigation apparatus as defined in claim 1 wherein the at least one field sensor includes a plurality of field sensors associated with the medical instrument.

33. The medical navigation apparatus as defined in claim 1 wherein the ascertained positions of the at least one field sensor are three-dimensional positions of the at least one field sensor.

34. The medical navigation apparatus as defined in claim 33 wherein the display is operable to display the three-dimensional ascertained positions of the at least one field sensor using color coding.

35. The medical navigation apparatus as defined in claim 1 wherein the medical instrument is a catheter and the at least one field sensor is encapsulated within the catheter.

36. The medical navigation apparatus as defined in claim 1 further comprising an X-ray imaging device operable to generate an X-ray image of the anatomical body where the medical instrument is being navigated.

37. The medical navigation apparatus as defined in claim 36 wherein the X-ray image obtained from the X-ray imaging device is correlated with the display representations of the position of the at least one field sensor associated with the medical instrument.

38. The medical navigation apparatus of claim 1, wherein the continuous representation from a plurality of perspectives includes a display operable to display the continuous representation from a plurality of perspectives to determine three-dimensional spacing between different portions of the continuous representations of the positions.

39. A medical navigation apparatus for navigating an anatomical body during a medical procedure, the medical navigation apparatus comprising:
a medical instrument operable to be navigated through the anatomical body during a medical procedure;
at least one magnetic field source associated with the medical instrument and operable to be moved in association with the medical instrument, the at least one magnetic field source further operable to radiate at least one magnetic field out of the anatomical body;
at least one field sensor operable to detect the at least one magnetic field from the at least one magnetic field source;
a controller operable to receive from the at least one field sensor signals indicative of the at least one magnetic field and operable to continuously ascertain positions of the at least one field source based upon the at least one magnetic field detected by the at least one field sensor; and
a display operable to continuously display representations of the position of the at least one field source associated with the medical instrument as it moves from a first position to a second position, wherein the continuous representations include a representation of the first position, a representation of the second position, and representations of the positions between the first position and the second position;
wherein the display is operable to display the three-dimensional ascertained positions of the at least one field source where at least a first color and a second color are used to define the continuous representations to indicate a relative position of a portion of the continuous representations to a point.

40. The medical navigation apparatus as defined in claim 39 wherein the medical instrument is selected from a group comprising a catheter, an endoscope, a colonoscope, and a combination thereof.

41. The medical navigation apparatus defined in claim 39 wherein the medical instrument is used for a cardiac medical procedure.

42. The medical navigation apparatus as defined in claim 39 wherein the at least one field sensor includes a single sensing coil.

43. The medical navigation apparatus as defined in claim 39 wherein the at least one field sensor is a flux gate magnetometer.

44. The medical navigation apparatus as defined in claim 39 wherein the at least one field sensor includes three sensing coils oriented orthogonal to one another about a common origin.

45. The medical navigation apparatus as defined in claim 39 wherein the at least one magnetic field is a quasi-static magnetic field.

46. The medical navigation apparatus as defined in claim 39 wherein the medical procedure is selected from a group comprising a colonoscopy, a bronchoscopy, a gastroscopy, a nasogastric procedure, an endotracheal procedure, cardiovascular procedure, and a combination thereof.

47. The medical navigation apparatus as defined in claim 39 wherein the at least one magnetic field source includes one field coil.

48. The medical navigation apparatus as defined in claim 39 wherein the at least one magnetic field source includes three field coils oriented orthogonal to one another about a common origin.

49. The medical navigation apparatus as defined in claim 39 wherein the display is further operable to simultaneously display local information corresponding to an area in the anatomical body where the at least one field source is located while displaying the representation of the ascertained position of the at least one field source.

50. The medical navigation apparatus as defined in claim 49 wherein the local information is an image.

51. The medical navigation apparatus as defined in claim 39 wherein the at least one magnetic field is a near-field electromagnetic field.

52. The medical navigation apparatus as defined in claim 39 wherein the controller is operable to calculate from the signals a location, an elevation angle and a rotation angle of the at least one field source.

53. The medical navigation apparatus as defined in claim 39 wherein continuously displaying representations further includes displaying a three-dimensional map formed based on the representations.

54. The medical navigation apparatus as defined in claim 53 wherein contours of the anatomical body are displayed as a three-dimensional map.

55. The medical navigation apparatus as defined in claim 53 wherein the display is operable to simultaneously display an actual image of an internal structure of the anatomical body with the three-dimensional map.

56. The medical navigation apparatus as defined in claim 39 wherein the at least one field source is attached to the medical instrument and moves with the medical instrument.

57. The medical navigation apparatus as defined in claim 39 wherein the at least one field source moves independent of the medical instrument.

58. The medical navigation apparatus as defined in claim 39 wherein the ascertained positions of the at least one field source are three-dimensional positions of the at least one field source.

59. The medical navigation apparatus as defined in claim 39 wherein the medical instrument is a catheter and the at least one field source is encapsulated within the catheter.

60. The medical navigation apparatus as defined in claim 39 wherein the representations of the position of the at least one field source may be rotated in any direction on the display.

61. The medical navigation apparatus as defined in claim 60 wherein the x-ray image obtained form the x-ray imaging device is correlated with the displayed representations of the position of the at least one field source associated with the medical instrument.

62. The medical navigation apparatus as defined in claim 39 further comprising an x-ray imaging device operable to generate an x-ray image of the anatomical body where the medical instrument is being navigated.

63. A medical navigation apparatus for navigating in an anatomical body during a medical procedure, the medical navigation apparatus comprising:
a medical instrument operable to be navigated through the anatomical body during the medical procedure;
at least one field sensor associated with the medical instrument and operable to be moved in association with the medical instrument;
at least three magnetic field sources operable to radiate at least three magnetic fields into the anatomical body, where each magnetic field has a moment different from each moment of each of the other two magnetic fields relative to a fixed point in space, each magnetic field operable to be detected by the at least one field sensor;
a controller operable to receive from the at least one field sensor signals indicative of the at least three magnetic fields and operable to ascertain a position of the at least one sensor based upon the at least three magnetic fields detected by the at least one field sensor; and
a display operable to simultaneously display a representation of the ascertained position of the at least one field sensor and local information corresponding to an area in the anatomical body where the at least one field sensor is located;
wherein the representation of the ascertained position of the at least one field sensor includes at least a first color and a second color to distinguish positions of two portions of the representations relative to a point.

64. The medical navigation apparatus as defined in claim 63 wherein the local information is an image.

65. The medical navigation apparatus as defined in claim 63 wherein the at least one field sensor is a single coil sensor.

66. The medical navigation apparatus as defined in claim 63 wherein the displayed representation reflects the ascertained position in three-dimensions.

67. The medical navigation apparatus as defined in claim 63 wherein the medical instrument is selected from a group comprising a catheter, an endoscope, a colonoscope, and a combination thereof.

68. The medical navigation apparatus as defined in claim 63 wherein at least one field sensor is a flux gate magnetometer.

69. The medical navigation apparatus as defined in claim 63 wherein the at least one field sensor includes three sensing coils that are orthogonal to one another about a common origin.

70. The medical navigation apparatus as defined in claim 63 wherein at least one magnetic field is a quasi-static magnetic field.

71. The medical navigation apparatus as defined in claim 63 wherein the medical procedure is selected from a group comprising a colonoscopy, a bronchoscopy, a gastroscopy, a nasogastric procedure, an endotracheal procedure, cardiovascular procedure, and a combination thereof.

72. The medical navigation apparatus as defined in claim 63 wherein the at least three magnetic field sources each include at least two coils formed orthogonally to one another about a common origin and are positioned at known locations in a two-dimensional plane.

73. The medical navigation apparatus as defined in claim 63 wherein the ascertained positions include both the location and orientation of the at least one field sensor associated with the medical instrument.

74. The medical navigation apparatus as defined in claim 63 wherein the controller is further operable to continuously ascertain positions of the at least one field sensor based upon the at least three magnetic fields detected by the at least one field sensor; and
the display is further operable to continuously display representations of the position of the at least one field sensor associated with the medical instrument as it moves from a first position to a second position, wherein the continuous representations include a representation of the first position, a representation of the second position, and representations of the positions between the first position and the second position.

75. The medical navigation apparatus as defined in claim 63 wherein contours of the anatomical body are displayed as a three-dimensional map.

76. The medical navigation apparatus as defined in claim 63 wherein the display is operable to simultaneously display an actual image of an internal structure of the anatomical body with the three-dimensional map.

77. The medical navigation apparatus as defined in claim 63 wherein the at least one field sensor moves independent of the medical instrument.

78. The medical navigation apparatus as defined in claim 63 wherein the at least one field sensor is attached to the medical instrument and moves with the medical instrument.

79. The medical navigation apparatus as defined in claim 63 wherein the at least one field sensor includes a plurality of field sensors associated with the medical instrument.

80. The medical navigation apparatus as defined in claim 63 wherein the ascertained position of the at least one field sensor are three-dimensional positions of the at least one field sensor.

81. The medical navigation apparatus as defined in claim 80 wherein the display is operable to display the three-dimensional ascertained positions of the at least one field sensor using color coding.

82. The medical navigation apparatus as defined in claim 63 further comprising an x-ray imaging device operable to generate an x-ray image of the anatomical body where the medical instrument is being navigated.

83. The medical navigation apparatus as defined in claim 82 wherein the x-ray image obtained from the x-ray imaging device is correlated with the display representation of the position of the at least one field sensor associated with the medical instrument.

84. A medical navigation apparatus for navigating an anatomical body during a medical procedure, the medical navigation apparatus comprising:
a medical instrument operable to be navigated through the anatomical body during the medical procedure;
at least one field sensor associated with the medical instrument and operable to be moved in association with the medical instrument;
at least one magnetic field source operable to radiate at least one magnetic field into the anatomical body and operable to be detected by the at least one field sensor;

a controller operable to receive from the at least one field sensor signals indicative of the at least one magnetic field and operable to continuously ascertain positions of the at least one field sensor based upon the at least one magnetic field detected by the at one least field sensor; and a display operable to continuously display representations of the position of the at least one field sensor associated with the medical instrument as it moves from a first position to a second position, wherein the continuous representations include a representation of the first position, a representation of the second position, and representations of the positions between the first position and the second position wherein the continuous representations of the position of the at least one field sensor is operable to be rotated in any direction on the display to illustrate the continuous representations from a plurality of perspectives of the continuous representations;

wherein the at least one magnetic field source includes a first magnetic field source operable to generate a first magnetic field, a second magnetic field source operable to generate a second magnetic field and a third magnetic field source operable to generate a third magnetic field wherein each of the first magnetic field source, the second magnetic field source, and the third magnetic field source each is a coil positioned orthogonally to the others about a first common origin.

85. The medical navigation apparatus of claim 84, further comprising a fourth magnetic field source, a fifth magnetic field source, and a sixth magnetic field source, each defined by a coil positioned orthogonally about a second common origin; a seventh magnetic field source, an eighth magnetic field source, and a ninth magnetic field source each defined by a coil positioned orthogonally about a third common origin;

wherein each of the first common origin, the second common origin, and the third common origin, are positioned substantially in a two-dimensional plane.

* * * * *